United States Patent
Swerdloff

(10) Patent No.: US 11,247,071 B2
(45) Date of Patent: Feb. 15, 2022

(54) METHOD OF PROVIDING PROTON RADIATION THERAPY UTILIZING PERIODIC MOTION

(71) Applicant: Elekta, Inc., Atlanta, GA (US)

(72) Inventor: Stuart Julian Swerdloff, Dunedin (NZ)

(73) Assignee: Elekta, Inc., Atlanta, GA (US)

( * ) Notice: Subject to any disclaimer, the term of this patent is extended or adjusted under 35 U.S.C. 154(b) by 0 days.

(21) Appl. No.: 16/397,619

(22) Filed: Apr. 29, 2019

(65) Prior Publication Data

US 2020/0338364 A1 Oct. 29, 2020

Related U.S. Application Data

(63) Continuation of application No. PCT/US2019/029380, filed on Apr. 26, 2019.

(51) Int. Cl.
*A61N 5/10* (2006.01)

(52) U.S. Cl.
CPC .......... *A61N 5/1037* (2013.01); *A61N 5/1081* (2013.01); *A61N 2005/1087* (2013.01)

(58) Field of Classification Search
None
See application file for complete search history.

(56) References Cited

U.S. PATENT DOCUMENTS

| 6,504,899 | B2 | 1/2003 | Pugachev et al. |
| 7,834,336 | B2 | 11/2010 | Boeh et al. |
| 8,093,568 | B2 | 1/2012 | Mackie et al. |
| 8,173,981 | B2 | 5/2012 | Trbojevic |
| 8,229,068 | B2 | 7/2012 | Lu et al. |
| 8,536,547 | B2 | 9/2013 | Maurer, Jr. et al. |
| 8,670,523 | B2 | 3/2014 | Yan et al. |
| 10,166,408 | B2 | 1/2019 | Michaud et al. |
| 2004/0254492 | A1 | 12/2004 | Zhang et al. |
| 2010/0183120 | A1 | 7/2010 | Nord et al. |
| 2011/0200170 | A1 | 8/2011 | Nord et al. |
| 2015/0360052 | A1* | 12/2015 | Martin ................ A61N 5/1075 378/65 |
| 2018/0185671 | A1* | 7/2018 | Filiberti ............... A61N 5/1069 |

(Continued)

FOREIGN PATENT DOCUMENTS

| EP | 3549636 A1 | 10/2019 |
| JP | 2007525249 A | 9/2007 |
| WO | WO-2015059576 A2 | 4/2015 |

(Continued)

OTHER PUBLICATIONS

"International Application Serial No. PCT/US2019/029380, International Search Report dated Aug. 19, 2019", 4 pgs.

(Continued)

*Primary Examiner* — Andrew Smyth
(74) *Attorney, Agent, or Firm* — Schwegman Lundberg & Woessner, P.A.; Sanjay Agrawal

(57) ABSTRACT

Techniques are described herein for delivering a particle beam from a continuously rotating gantry towards a target according to a determined patient state. The determined patient state and an identified gantry angle of a gantry may be used to deliver a set of beamlets (e.g., a pattern of radiation dose) to the target. The particle beam may rotate through a range of gantry angles. The set of beamlets may be delivered continuously while the gantry rotates.

22 Claims, 15 Drawing Sheets

(56) References Cited

U.S. PATENT DOCUMENTS

2019/0099620 A1* 4/2019 Isola .................... A61N 5/1067
2019/0111284 A1* 4/2019 Lee ...................... A61B 6/4258

FOREIGN PATENT DOCUMENTS

WO    WO-2019154605 A1    8/2019
WO    WO-2019164835 A1    8/2019

OTHER PUBLICATIONS

"International Application Serial No. PCT/US2019/029380, Invitation to Pay Additional Fees dated Jun. 27, 2019", 2 pgs.
"International Application Serial No. PCT/US2019/029380, Written Opinion dated Aug. 19, 2019", 6 pgs.
"Australian Application Serial No. 2019359621, First Examination Report dated Dec. 10, 2020", 4 pgs.
Battinelli, Cecilia, "Proton Arc Therapy Optimization", Royal Institute of Technology School of Engineering Sciences, (2019), 94 pgs.
Cao, Wenhua, et al., "Proton energy optimization and reduction for intensity-modulated proton therapy", Phys.Med. Biol. 59, (2014), 15 pgs.
Ding, Xuanfeng, et al., "Have we reached proton beam therapy dosimetric limitations?—A novel robust, delivery-efficient and continuous spot-scanning proton arc (SPArc) therapy is to improve the dosimetric outcome in treating prostate cancer", Acta Oncologica, (Aug. 3, 2017), 4 pgs.
Freeman, Tami, "Proton arc therapy: the next evolution in proton delivery?", Physics World, (Oct. 16, 2019), 3 pgs.
Kabolizadeh, Peyman, et al., "Defining The Future of Radiation Oncology: Latest Updates on Proton Arc Therapy", Beaumont, (Nov. 11, 2018), 14 pgs.
Kohno, Ryosuke, et al., "Development of Continuous Line Scanning System Prototype for Proton Beam Therapy", International Journal of Particle Therapy, (2017), 10 pgs.
Kraus, Kim Melanie, "Dose Delivery Study for a Novel Compact Proton Accelerator", Dissertation, (Jan. 15, 2014), 143 pgs.
Yi, Byong Yong, et al., "Proton Arc Therapy with Modulating Proton Energies", University of Maryland Ventures, (May 1, 2018), 3 pgs.
"European Application Serial No. 19926335.1, Response to Communication pursuant to Rules 161(2) and 162 EPC filed May 31, 2021", 22 pgs.
"European Application Serial No. 19926335.1, Extended European Search Report dated Dec. 6, 2021", 5 pgs.

* cited by examiner

COUNTER-CLOCKWISE SPIRAL

CLOCKWISE SPIRAL

0 DEGREE BEAM + 315 DEGREE BEAM + 90 DEGREE BEAM

METHOD OF PROVIDING PROTON RADIATION THERAPY UTILIZING PERIODIC MOTION

CLAIM FOR PRIORITY

This application is a continuation of and claims the benefit of priority to International Application No. PCT/US2019/029380, filed Apr. 26, 2019, which is hereby incorporated by reference in its entirety.

BACKGROUND

Radiation therapy or "radiotherapy" may be used to treat cancers or other ailments in mammalian (e.g., human and animal) tissue. One such radiotherapy technique is referred to as "gamma knife," by which a patient is irradiated using a number of lower-intensity gamma rays that converge with higher intensity and high precision at a targeted region (e.g., a tumor). In another example, radiotherapy is provided using a linear accelerator ("linac"), whereby a targeted region is irradiated by high-energy particles (e.g., electrons, high-energy photons, and the like). In another example, radiotherapy is provided using a heavy charged particle accelerator (e.g. protons, carbon ions, and the like), The placement and dose of the radiation beam is accurately controlled to provide a prescribed dose of radiation to the targeted region. The radiation beam is also generally controlled to reduce or minimize damage to surrounding healthy tissue, such as may be referred to as "organ(s) at risk" (OARs). Radiation may be referred to as "prescribed" because generally a physician orders a predefined dose of radiation to be delivered to a targeted region such as a tumor.

Generally, ionizing radiation in the form of a collimated beam is directed from an external radiation source toward a patient. Modulation of a radiation beam may be provided by one or more attenuators or collimators (e.g., a multi-leaf collimator). The intensity and shape of the radiation beam may be adjusted by collimation avoid damaging healthy tissue (e.g., OARs) adjacent to the targeted tissue by conforming the projected beam to a profile of the targeted tissue.

The treatment planning procedure may include using a three-dimensional image of the patient to identify the target region (e.g., the tumor) and such as to identify critical organs near the tumor. Creation of a treatment plan may be a time consuming process where a planner tries to comply with various treatment objectives or constraints (e.g., dose volume histogram (DVH) objectives or other constraints), such as taking into account importance (e.g., weighting) of respective constraints in order to produce a treatment plan that is clinically acceptable. This task may be a time-consuming trial-and-error process that is complicated by the various organs at risk (OARs) because as the number of OARs increases (e.g., about thirteen for a head-and-neck treatment), so does the complexity of the process. OARs distant from a tumor may be more easily spared from radiation, but OARs close to or overlapping a target tumor may be more difficult to spare from radiation exposure during treatment.

Generally, for each patient, an initial treatment plan may be generated in an "offline" manner. The treatment plan may be developed well before radiation therapy is delivered, such as using one or more medical imaging techniques. Imaging information may include, for example, images from X-rays, Computed Tomography (CT), nuclear magnetic resonance (MR), positron emission tomography (PET), single-photon emission computed tomography (SPECT), or ultrasound. A health care provider, such as a physician, may use three-dimensional imaging information indicative of the patient anatomy to identify one or more target tumors along with the organs at risk near the tumor. The health care provider may delineate the target tumor that is to receive a prescribed radiation dose using a manual technique, and the health care provider may similarly delineate nearby tissue, such as organs, at risk of damage from the radiation treatment.

Alternatively or additionally, an automated tool (e.g., ABAS® provided by Elekta AB, Sweden) may be used to assist in identifying or delineating the target tumor and organs at risk. A radiation therapy treatment plan ("treatment plan") may then be created using an optimization technique based on clinical and dosimetric objectives and constraints (e.g., the maximum, minimum, and mean doses of radiation to the tumor and critical organs).

The treatment planning procedure may include using a three-dimensional image of the patient to identify the target region (e.g., the tumor) and to identify critical organs near the tumor. Image acquisition may be performed just before initiation of delivery of a specified radiation therapy fraction. Such imaging may provide information helpful for identifying a position of a target region or for identifying motion of the target region. Such contemporaneous imaging may be referred to generically as "real-time," but in general a latency or time delay exists between an acquisition of an image and a delivery of radiation therapy.

The treatment plan may then be later executed by positioning the patient and delivering the prescribed radiation therapy. The radiation therapy treatment plan may include dose "fractioning," whereby a sequence of radiation therapy deliveries are provided over a predetermined period of time (e.g., 45 fractions or some other total count of fractions), such as with each therapy delivery including a specified fraction of a total prescribed dose. During treatment, the position of the patient or the position of the target region in relation to the treatment beam is important because such positioning in part determines whether the target region or healthy tissue is irradiated.

In one approach, radiation therapy may be provided by using particles, such as protons, instead of electrons. This typically may be referred to as proton therapy. One significant known advantage of proton therapy is it provides superior dose distribution with minimal exit dose compared to other forms of radiation therapy, such as x-ray therapy. There is a significant reduction of dose to organs at risk (OAR) because of the minimal exit dose. Further advantages include lower dose per treatment, which lowers the risk of side effects and may improve quality of life during and after proton therapy treatment.

One method of providing proton therapy is to use a broad proton beam, such as a spread-out Bragg peak that provides a uniform beam having multiple energies. If rotational therapy is to be used to treat the patient, it may not be accomplished using a broad beam. For example, a broad beam requires an ion beam compensator per treatment field customized per patient. This means there would be one compensator required for every angle, therefore, multiple compensators would have to be used to treat a patient. For instance, for at least every 4 degrees, a different compensator would have to be used. Treatment would have to be stopped and started using 90 different ion compensators to provide a 360 degree rotational proton radiation therapy. Another issue with using a broad beam is there is an undesired shape to the dose at the proximal edge of the targeted tumor.

Definitions

A spot is a location that is configured to a diameter of a beamlet that is to be delivered to that location.

A beamlet comprises a stream of particles having a nominal diameter delivered at a predetermined rate to a starting point and to an ending point.

A line segment is configured to uniformly deliver a plurality of particles between a starting position and an ending position.

OVERVIEW

In one approach, a method of delivering a particle beam from a continuously rotating gantry towards a target, where the particle beam is composed of a plurality of beamlets and the target is moving according to a periodic cycle. An illustrative example of such a method includes determining a periodic cycle, identifying a corresponding radiation therapy treatment plan, and selecting a set of beamlets for the periodic cycle corresponding to an angle of rotation of a gantry, and optionally delivering the particle beam in a rotational pattern.

This overview is intended to provide an overview of subject matter of the present patent application. It is not intended to provide an exclusive or exhaustive explanation of the invention. The detailed description is included to provide further information about the present patent application.

Figure 1:
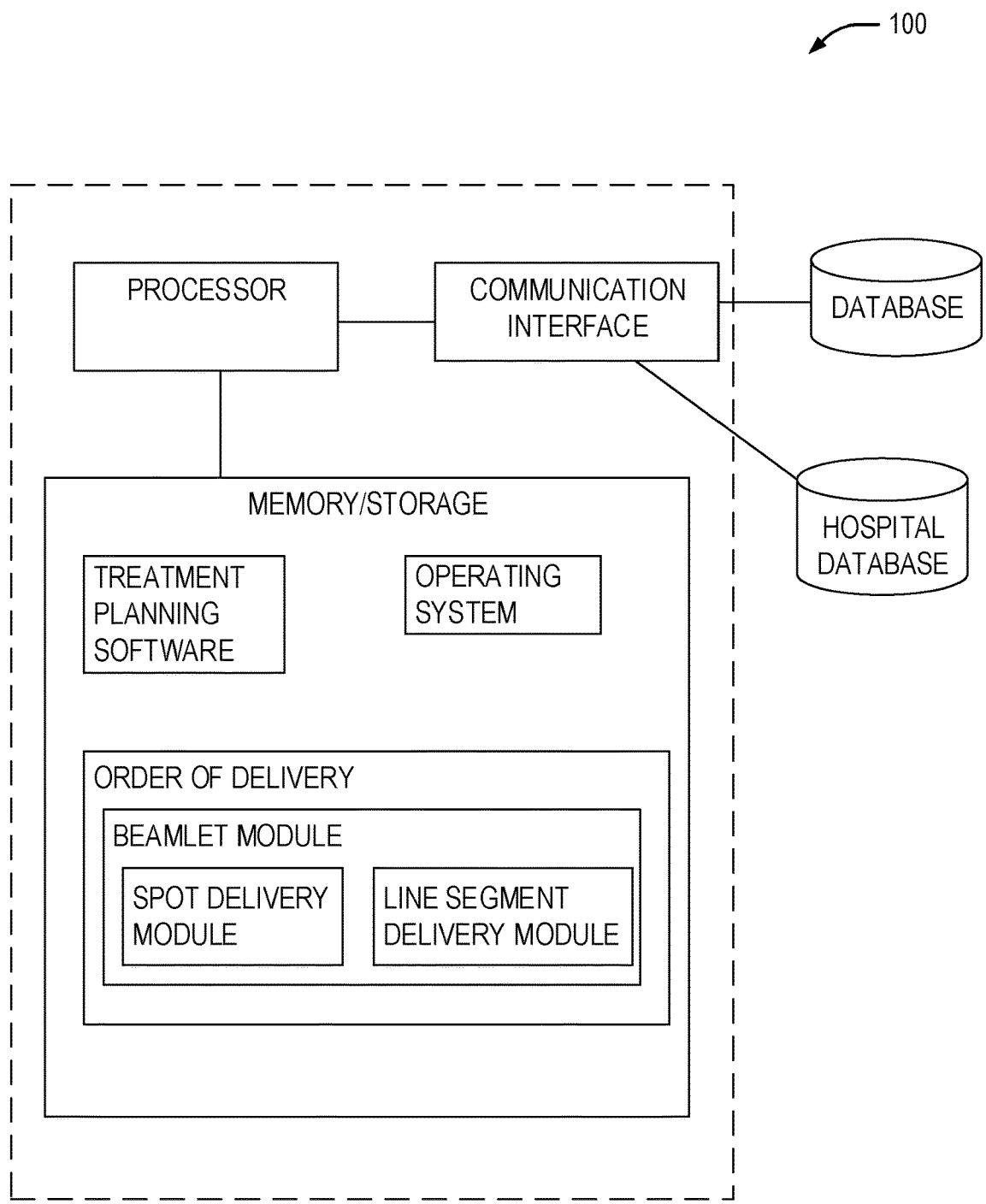
FIG. 1 illustrates generally an example of a system, such as may include a particle therapy system controller, in accordance with an embodiment.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods described herein provide radiation therapy to a patient. The radiation therapy is provided with a rotating gantry, for example by a particle beam affixed to the gantry. The gantry may continuously rotate while the particle beam applies a plurality of beamlets. The beamlets may be applied in a spiral pattern on a target (e.g., a tumor or a portion of a tumor or other spot). In an example, rotating the gantry while delivering the particle beam may be inefficient (e.g., if dosage and penetration information for every degree or half degree is planned). In another example, rotating the gantry may introduce errors (e.g., if every few degrees are planned, such as every five or ten degrees). There are a number of advantages of providing rotational proton radiation therapy. First, instead of an undesired entrance dose at a small number of angles, the dose may be delivered from many angles.

The systems and methods described herein account for both of these issues by introducing a spiral pattern for delivery of the beamlets. The spiral pattern may be used with planned angles at a range of degrees (e.g., five, ten, fifteen, etc.). In an example, the spiral pattern may include delivering the particle beam to a central portion of the target when at a highest error and to an outer portion of the target when at a lowest error. The amount of error may depend on angle difference between the actual gantry angle and the planned angle, for example with a higher error corresponding to a larger difference between angles, and a lower error corresponding to a smaller difference between angles.

In an example, a spiral pattern for applying a particle beam to a target may decrease time needed to complete a radiation therapy treatment. For example, beamlet size of beamlets delivered during the treatment may vary. To change size of the beamlets may cause disruption to treatment, for example by taking time or using energy. Using a raster type pattern may require multiple changes in beamlet size. Using the spiral pattern may allow for as few as a single change in beamlet size. For example, smaller beamlets may be used on an outside edge of a target, while larger beamlets may be used on an inside portion of the target.

One challenge occurs with accurately tracking a target, OAR, or other objects, when the patient is moving. Movement may be classified as either cyclical (e.g., breathing or heartbeat) or non-cyclical. Cyclical breathing presents a unique problem when a target for treatment is affected by movement of the patient. A set of phases for a periodic cycle may be defined, for example 8 or 16 unique phases within the periodic cycle. Other sets of phases may be used, for example, anywhere from 2 to 20. The phases may represent positions through the periodic cycle that are repeated with each iteration through the cycle.

Using phases of a periodic cycle, a radiation dose may be generated for treatment of a target at each of the phases. Treating a moving target may use the phases to ensure proper coverage of the target, but doing so may result in a dose to normal healthy tissue or any organ at risk. A non-rotating device typically has a fixed angle for delivery of particles to the target. One approach to ensure the dose is delivered to the moving target is to pause delivery of the beam (e.g., "gate" the beam) when the target is not near its nominal (typically "at rest" near the end of either exhalation or inhalation) position. Thus, only one phase of the cycle is targeted, and the dosage is only applied during that phase.

However, when using a non-rotating particle therapy device a plurality of layers from the fixed angle aggregate to cover the entire target. This can result in increased dosage to healthy tissue, an organ at risk, or particularly skin around an entry point. Thus a rotating gantry may be used to avoid the increased dosage to the skin or other tissue resting in the delivery line between a beam emitter and the target. When using a rotating gantry and providing a rotational delivery of particles, delivery of the beam typically cannot be paused without either stopping rotation of the gantry or missing the range of angles covered by the rotation. The solution for a non-rotating gantry that relies on stopping the beam does not work with a rotating gantry.

The systems and methods described herein deliver a dosage while a gantry continuously rotates, without stopping the gantry, and during phase changes in a periodic cycle by using a spiral delivery technique based on a patient's current phase and a gantry angle (or range of gantry angles).

Instead of attempting to deliver all layers of the tumor from each angle, one or two layers that are past the middle of the target or prior to the middle of the target may be used. A layer may include a depth location to be aimed at within a target. Multiple angles of delivery of the particles to the target may be used, such as by continuously rotating the gantry. Because the target is in periodic cyclical motion, and may be in periodic motion with the periodic breathing of the patient, a set of parameters may be used that correspond to a given breath phase and the angle of delivery of the particles to deliver dose to the intended part of the target.

A database or other storage of sets of parameters may be used, with each set of parameters including a particular breath phase, a particular gantry angle, and a particular dose of particles. In an example, the particular gantry angle may include a range of angles. For example, the sets of parameters may correspond to every 5 or 10 degrees of angles (e.g., 72 or 36 angles). Each of the angles specified may be matched with each of the phases of a cycle. For example, with 8 phases in a breathing cycle and 36 angles (with, for example, a 10 degree range), a total of 288 radiation doses or sets of beamlets may be generated or stored. The generation of doses or beamlets may occur before treatment. In another example, with 16 phases and 72 angles (a 5 degree range), 1,152 radiation doses or sets of beamlets may be generated or stored. During treatment, a current phase and a current gantry angle may be identified and the corresponding radiation doses or sets of beamlets may be selected.

An accumulated dose to the target using a rotating gantry may be equal to the weighted sum of all doses of particles from each of the angles, given the breath phase at each angle.

FIG. 1 illustrates generally an example of a system 100, such as may include a particle therapy system controller, in accordance with an embodiment. The system 100 may include a database or a hospital database. The particle therapy system controller may include a processor, communication interface, or memory. The memory may include treatment planning software, an operating system, or a delivery controller. The delivery controller may include a beamlet module for determining or planning spot delivery (e.g., using a spot delivery module) or line segment delivery (e.g., using a line segment delivery module).

In an example, the spot delivery module or the beamlet module may be configured to plan size of beamlets, location of a target or spot, or the like. The beamlet module may be used to determine an order of delivery of beamlets, for example in a spiral pattern as described herein. The order of delivery module may be in communication with the treatment planning software for planning delivery of beamlets. For example, the treatment planning software may be used to determine or plan gantry angle, gantry speed, beamlet size, spiral pattern (e.g., clockwise or counterclockwise), angle range for a particular spiral pattern (e.g., every ten degrees of the gantry rotation), or the like.

The processor may implement the plan, such as by communicating, via the communication interface or otherwise, to components used to implement the plan (e.g., to control devices or components, such as those described below with reference to FIG. 3). In an example, the communication interface may be used to retrieve stored information from a database or a hospital database (e.g., patient information, past procedure information for the patient or other patients, procedure instructions, information about particular devices or components, or the like).

Figure 2:
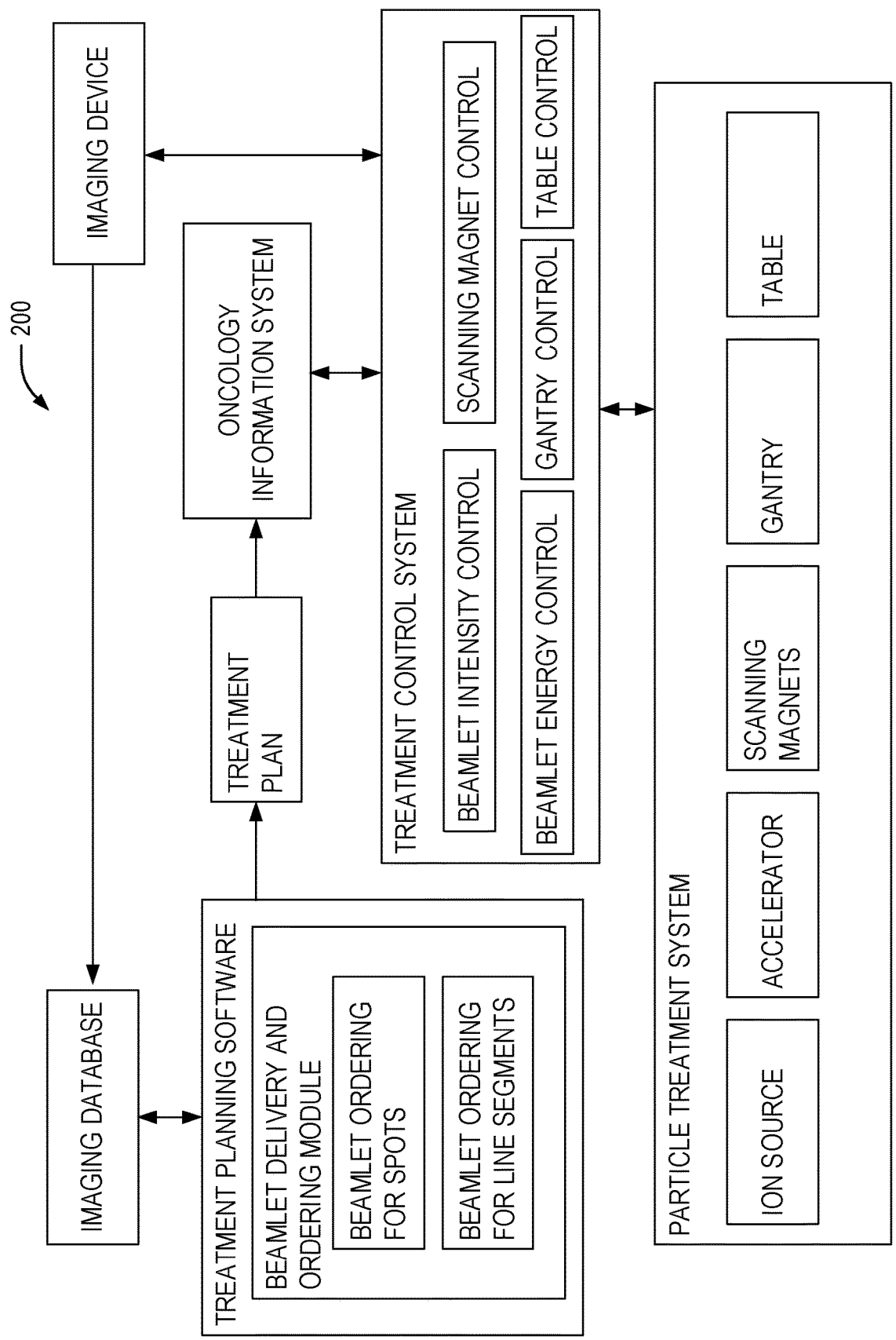
FIG. 2 illustrates generally an example of a radiation therapy system, such as may include a particle treatment system and an imaging acquisition device, in accordance with an embodiment.

FIG. 2 illustrates generally an example of a radiation therapy system 200, such as may include a particle treatment system and an imaging acquisition device, in accordance with an embodiment. The particle treatment system includes an ion source, an accelerator, and scanning magnets, each of which is described in more detail below with respect to FIG. 3. The particle treatment system includes a gantry and a table, where the gantry may be mounted on the table, affixed to the table, or stabilized with respect to the table. The table may hold a patient. The gantry may be a rotating gantry, and may rotate with respect to the table (e.g., around the table) or with respect to the patient (and the table or a portion of the table may rotate with the gantry).

The particle treatment system may communicate with a treatment control system, which may be used to control actions of the particle treatment system. The treatment control system may communicate with an imaging acquisition device (e.g., to receive images taken by the imaging acquisition device or an imaging database) or an oncology information system. The oncology information system may provide treatment plan details to the treatment control system, such as received from treatment planning system. The treatment control system may use the treatment plan to control the particle treatment system (e.g., activate the gantry, the ion source, the accelerator, the scanning magnets, a particle beam, or the like). The treatment control system, for example, may include a beamlet intensity control, a beamlet energy control, a scanning magnet control, a table control, a gantry control, etc. In an example, the beamlet intensity control and the beamlet energy control may be used to activate a beamlet of a particular size or to target a particular location. The scanning magnetic control may be used to deliver beamlets according to the treatment plan, for example in a spiral pattern. The gantry control or the table control may be used to rotate the gantry.

The treatment planning software may include components such as a beamlet delivery and ordering module, with, for example, separate controls for beamlet ordering for spots or line segments. The treatment planning software is described in more detail above with respect to FIG. 1. The treatment planning software may access an imaging database to retrieve images or store information. When a treatment plan is completed, the treatment planning software may send the plan to an oncology information system for communication with the treatment control system.

Figure 3:
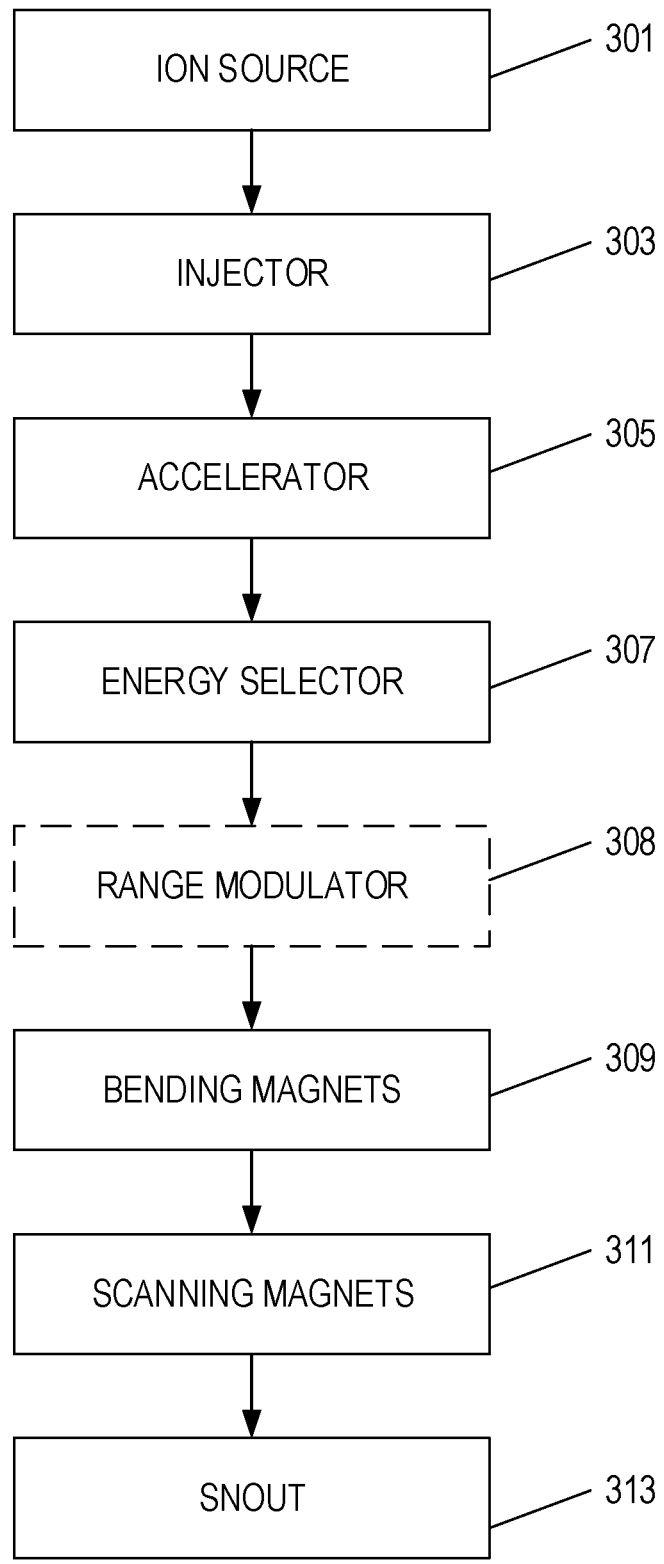
FIG. 3 illustrates generally a particle treatment system that may include a radiation therapy output configured to provide a proton therapy beam, in accordance with an embodiment.

FIG. 3 illustrates in an embodiment of a particle treatment system 300 that may include a radiation therapy output configured to provide a proton therapy beam. The particle treatment system 300 includes an ion source 301, an injector 303, an accelerator 305, an energy selector 307, a plurality of bending magnets 309, a plurality of scanning magnets 311, and a snout 313.

The ion source 301, such as a synchrotron (not shown) may be configured to provide a stream of particles, such as protons. The stream of particles is transported to an injector 303 that provides the charged particles with an initial acceleration using a Coulomb force. The particles are further accelerated by the accelerator 305 to about 10% of the speed of light. The acceleration provides energy to the particles, which determines the depth within tissue the particles may travel. The energy selector 307 (e.g., a range scatter) may be used to select the energies of the protons to be delivered to the patient. In an embodiment called passive scattering, an optional range modulator 308 (e.g., also called a ridge filter or a range modulation wheel) may be utilized to broaden the beam to fit the tumor. After selecting energies, a set of bending magnets 309 may be utilized to transport the stream of protons into a radiation therapy treatment room of a hospital. Further, scanning magnets 311 (e.g., x-y magnets) are used to spread the proton beam to, or trace, an exact image of the tumor shape. A snout 313 or components of the snout 313 (e.g., a collimation device) may be used to further shape the proton beam. In various embodiments, the stream of particles may be composed of carbon ions, pions, or positively charged ions.

Figure 4:
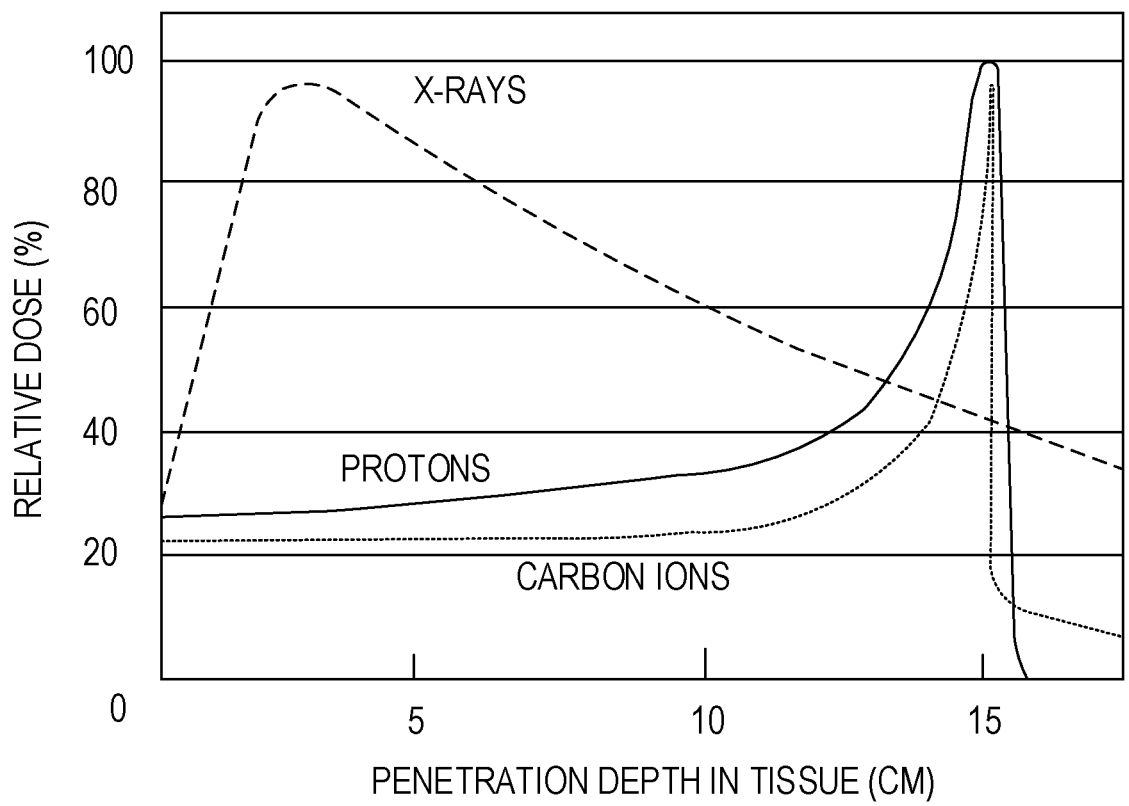
FIG. 4 illustrates generally radiation dose depths in human tissue for various types of particles, in accordance with an embodiment.

FIG. 4 provides an illustration of a comparison of radiation dose depths for various types of particles in human tissue. As shown, the relative depth of penetration into human tissue of photons (e.g., x-rays) versus protons versus carbon ions is provided (e.g., including any radiation dose provided at a distance beneath the surface, including secondary radiation or scatter). Each radiation dose is shown relative to the peak dose for a proton beam having a single energy which has been set to 100%.

The mono-energetic (e.g., single energy) proton beam indicates a plateau region starting at approximately 25% that gradually increases until approximately 10 cm depth in tissue where it rapidly increases to the Bragg Peak at 15 cm and then advantageously falls to zero within a short distance. No additional dose is delivered at the end of the Bragg peak.

The photon beam (e.g., labelled as X-rays) indicates the initial build up due to electron scatter (e.g., the primary means by which X-rays deliver dose to tissue is through transfer of energy to electrons in the tissue). This is followed by an exponential fall off, which continues past the distal edge of the target, which is at approximately 15 cm depth in the diagram. The x-ray beam has an entrance (skin) dose set to match that of the proton beam. With normalization (e.g., scaling) at 15 cm depth, the dose due to x-rays is at 40% of the dose provided by proton beam, while the x-ray beam has a peak dose of greater than 95% ("near" 100%) at approximately 3 cm depth. If the x-ray data is renormalized to achieve 100% dose at 15 cm, the peak dose at approximately 3 cm depth would be approximately 240%, in a location where dose is not desired (e.g., prior to the target). Therefore, with x-rays, a considerable amount of dose is delivered prior to the target and an appreciable amount of dose is delivered past the target.

The mono-energetic carbon beam shows a plateau region at the entrance dose that is lower than the proton beam. The carbon beam has a sharper Bragg Peak that falls more precipitously than the proton beam, but the carbon beam has a tail (e.g., known as a "spallation tail", where some of the Carbon nuclei shatter in to Helium ions) that has approximately 10% additional dose, or less, past the desired target by several centimeters. The carbon ion beam has an undesired entrance and skin dose compared to the proton beam, but the carbon ion beam has a non-trivial dose delivered past the target.

Figure 5:
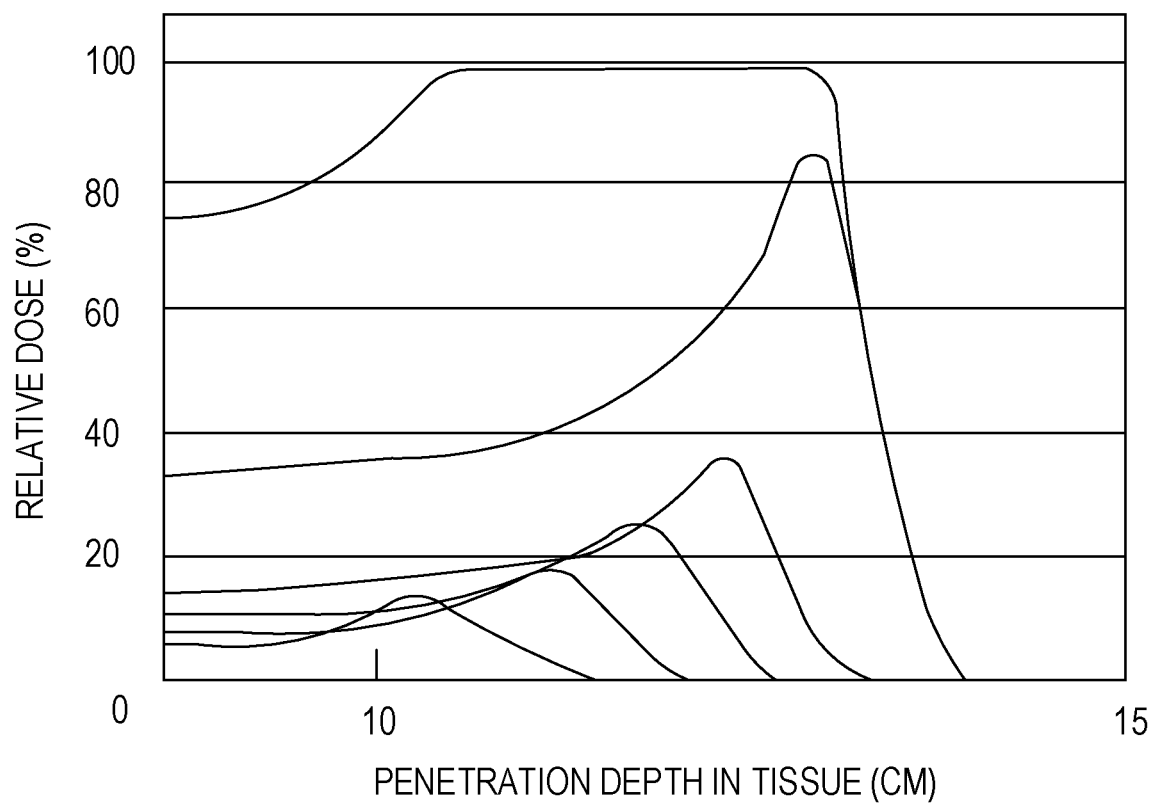
FIG. 5 illustrates generally a spread out Bragg Peak, in accordance with an embodiment.

FIG. 5 provides an illustration of a spread-out Bragg peak (SOBP). The SOBP. displays a relative depth dose curve for the combination of a set of proton beams of various initial energies each of which has had some spread in energy (e.g., variable absorption of energy in tissue). The desired result of having a uniform dose for a target of a particular thickness. As shown, the target is shown with a proximal depth of approximately 10 cm, a distal depth of approximately 13 cm, and a target thickness of approximately 3 cm. Within the target, the dose is quite uniform (with an average normalized at 100%). The diagram does not start at 0 cm depth and is not explicitly showing the entrance (skin) dose, but the nature of the entrance region of proton beams is a relatively flat depth dose curve. Typically, the entrance (skin) dose will be approximately 70% of the target dose (e.g., shown at the far right edge of the x-axis). A SOBP may be obtained using a variety of approaches, including using a scattered proton beam with modulation of the energy (variable absorption) utilizing a variety of devices (e.g., a static ridge filter or a dynamic range modulation wheel), or by selection of a number of mono-energetic proton beams that do not undergo scatter.

Figure 6:
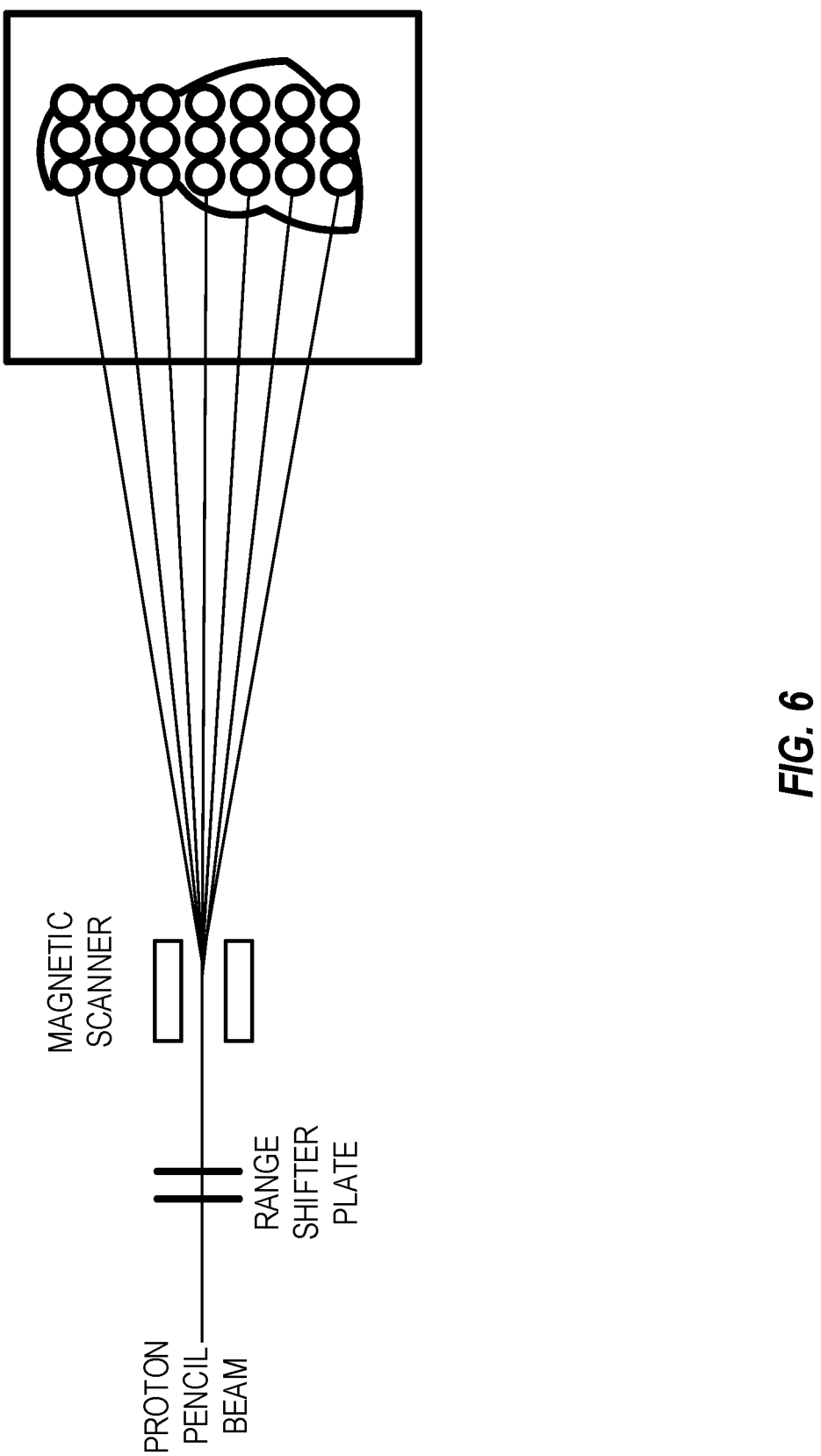
FIG. 6 illustrates generally a diagram of an active scanning proton beam delivery system, in accordance with an embodiment.

FIG. 6 provides an illustration of a diagrammatic representation of a typical active scanning proton beam delivery system. As shown, a single layer of a pencil beam scan is being delivered, with a grid of spots depicted on a patient in conjunction with a contour of the cross-sectional area to which particles are to be delivered. An incoming mono-energetic proton beamlet has a specified amount of its energy absorbed by the Range Shifter (e.g., in FIG. 6 it is a Range Shifter plate), resulting in a beamlet with the desired energy to achieve a certain depth for the Bragg Peak in the patient to treat the specified layer. A magnetic scanner, which has the ability to deflect the particles in both a vertical and a horizontal direction. The strength of the magnetic fields may be adjusted to control the deflection in the direction perpendicular to the magnetic field and the incoming beamlet. The rate at which the magnetic field strengths may be adjusted determines the rate at which the scanning may take place. For instance, the intensity of the proton beamlet in combination with the scanning rate determines how much dose may be delivered to a specific area (e.g., in FIG. 6, a "spot") in a particular amount of time (e.g., particles/unit area). In theory, the magnetic field strengths may be adjusted independently of each other (in a fashion similar to the children's toy "Etch a Sketch®", provided by Spin Master™, Toronto, Canada; with the pencil beamlet intensity being a variable not available in the children's toy). The most common scheme for scanning is to scan in one direction quickly and to scan in the perpendicular direction more slowly in a raster fashion, similar to how early televisions were controlled (e.g., Cathode Ray Tube (CRT), which use electrons instead of protons), but arbitrary patterns may be scanned (similar to the previously mentioned toy). Delivery of distinct spots is achieved by incrementing the scanning magnetic field strength and throttling the pencil beam intensity between increments.

Figure 7B:
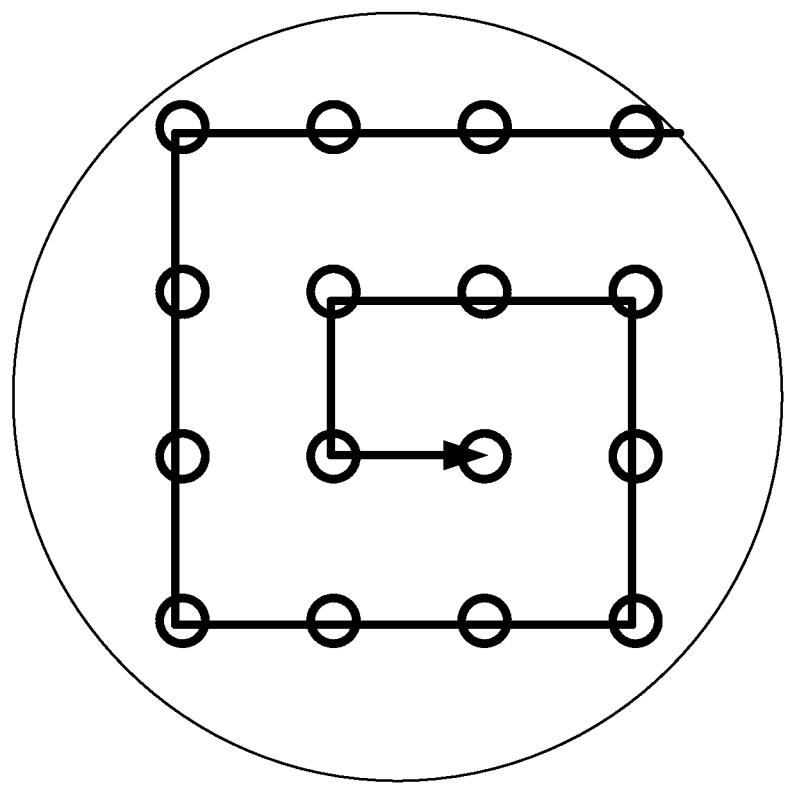
FIGS. 7A-7B illustrate generally spiral delivery paths on a grid, in accordance with an embodiment.
Figure 7A:
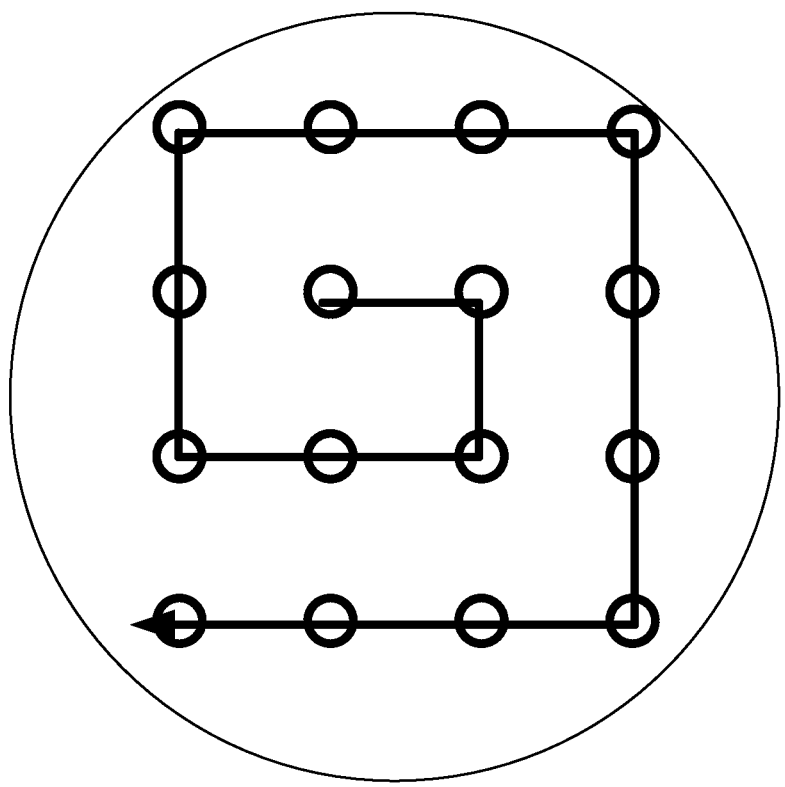

FIGS. 7A-7B illustrate generally spiral delivery paths on a grid, in accordance with an embodiment. The spiral patterns shown in FIGS. 7A-7B minimize the errors resulting from a rotating gantry. The spiral patterns shown improve target accuracy and decrease radiation outside the target compared to linear raster patterns while the gantry rotates.

The systems and methods described herein use proton arc therapy to optimize a radiation dose when delivering protons to certain spots. When delivering to certain spots, discrepancies may be minimized for what was planned versus what is actually delivered using the spiral pattern scan described herein. Unless the spots that are further from the isocentric axis are delivered while the gantry is closest to the current planned angle, the resulting actual spot location may be far from the intended spot location and the overall trajectory of the beamlet will differ significantly from the expected trajectory. Using a spiral scan minimizes the errors in the actual spot locations and minimizes the discrepancy between the expected and actual trajectories of the beamlets.

Figure 7C:
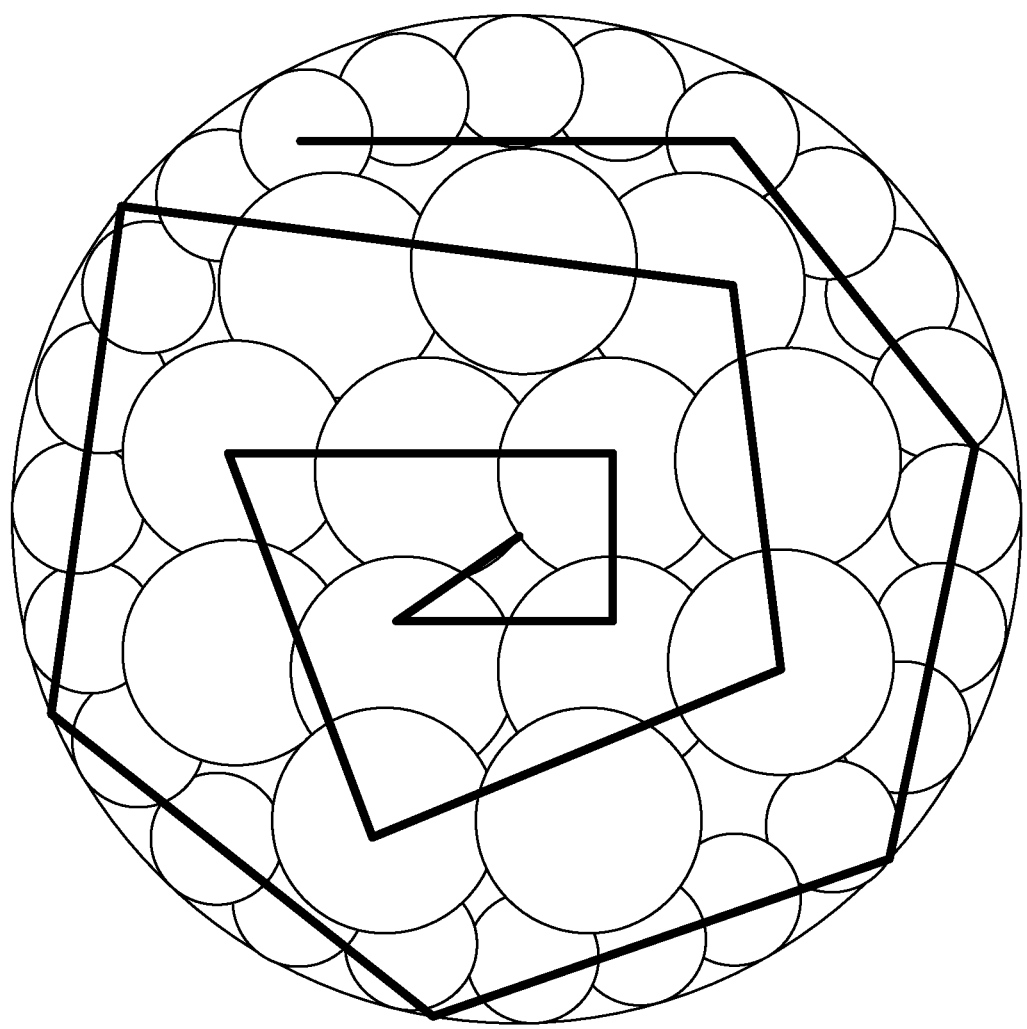
FIG. 7C illustrates a spiral spot delivery path with differing spot sizes, in accordance with an embodiment.

FIG. 7C illustrates a spiral spot delivery path with differing spot sizes, in accordance with an embodiment.

The trade-off between a small and large spot is that to only deliver small beamlets to a small spot takes an inordinate amount of time to deliver radiation therapy. Therefore, to decrease the time, it is better to deliver the small beamlets to the outer edges/exterior of the tumor and deliver larger spots to the interior of the tumor. Changing spot size during delivery is a time consuming activity. By using the spiral delivery pattern shown in FIG. 7C, there may be as few as a single transition in spot sizes when going from the set of smaller spots treating the outer edges of the tumor to the set of larger spots treating the inner region of the tumor. Similarly, there may be as few as a single transition in spot sizes when going in the reverse, resulting in only two changes in spot size for the entire beam. In an example, the spiral pattern may be a two-dimensional spiral pattern, delivering dosage at each layer of the target.

In an example, beamlets may be delivered at the edges of an arc range may while the spiral is in the center of the target. For example, in an arc from 0 degrees to 10 degrees, the target may be planned as if the gantry was stationary at 5 degrees. In this example, the outside of the spiral occurs as the gantry approaches and leaves 5 degrees, while the center of the spiral occurs as the gantry leaves 0 degrees and as the gantry approaches 10 degrees. For example, starting at 0 degrees, the spiral may begin at the center of the target and spiral outward until ending (at an outward point of the spiral) around 5 degrees. Then, in an example, the spiral may reverse (e.g., move clockwise from 0 to 5 degrees, then counter-clockwise from 5 to 10 degrees, or vice versa) on the way back to the center of the target as the gantry moves from 5 to 10 degrees. The process may be repeated on a different layer of the target at another arc, for example from 10 to 20 degrees, etc., until the dose is completed.

Figure 8:
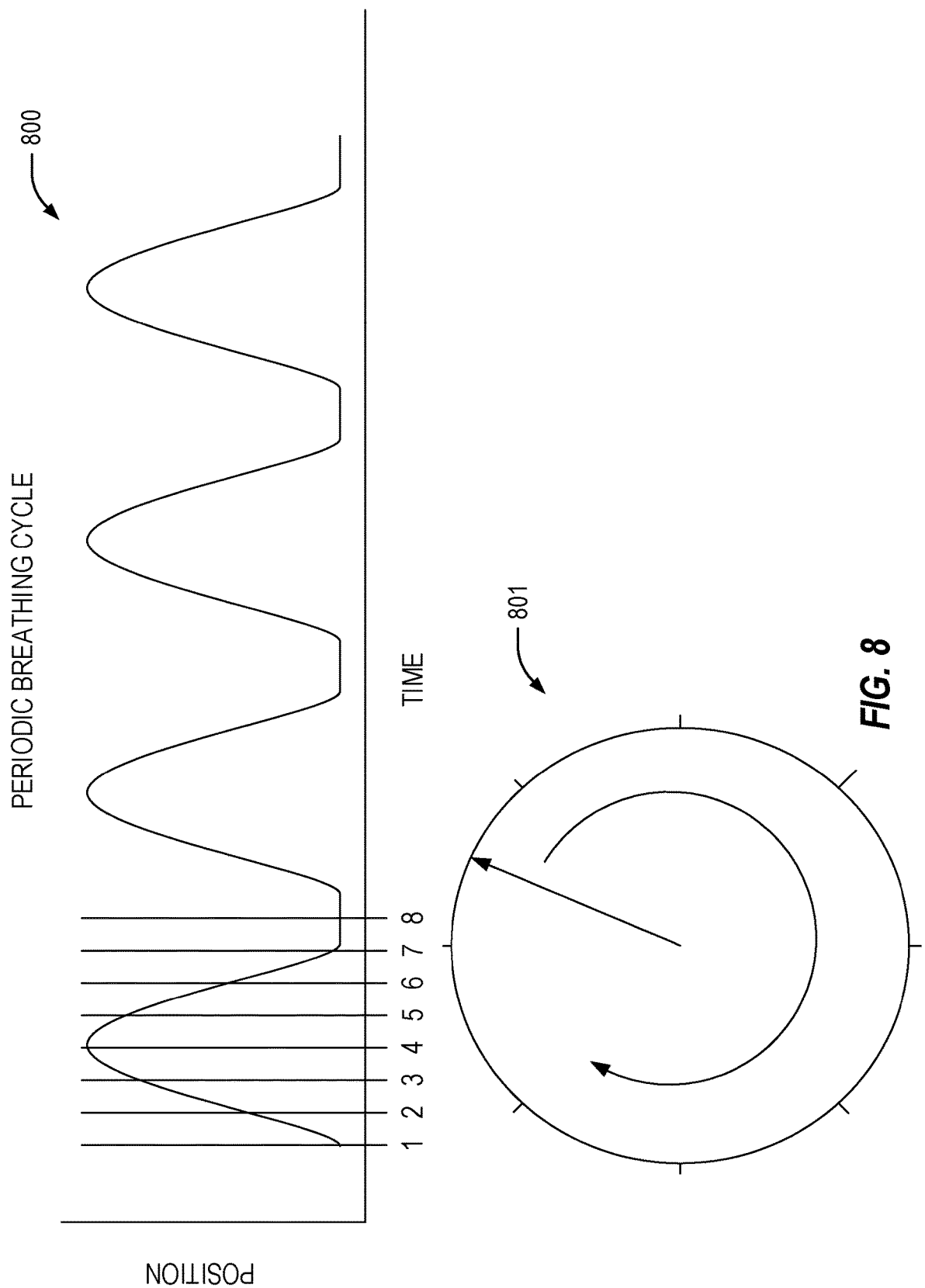
FIG. 8 illustrates example periodic phases of a patient, in accordance with an embodiment.

FIG. 8 illustrates example periodic phases of a patient, in accordance with an embodiment. A periodic breathing cycle 800 is illustrated with 8 phases (but may include other numbers (e.g., 16 phases). In an example, other patient state information may be used with the techniques described herein. For example, the patient state may be represented by a breathing phase, an approximation of a breathing phase, an amplitude, a deformation vector field (DVF), a low-dimensional representation of a DVF, a low-dimensional representation of images acquired with an imaging device, surface information, a target position, or the like.

The periodic breathing cycle 800 is represented by position over time, with position varying based on movement of lungs, throat, diaphragm, muscles, and other aspects of the respiratory system.

A gantry angle 801 is also illustrated with a current angle depicted as well as a direction of angular motion of the gantry. The gantry angle 801 represents movement of a gantry over time, and is used with the periodic breathing cycle to deliver a predetermined radiation dose to a patient.

The periodic breathing cycle 800 is periodic and the phases or states may repeat over time. A plan for each phase or state of a cycle may be developed for delivering a treatment dosage to a target near or affected by movement in the cycle. For example, for each phase or state, a radiation dose or set of beamlets may be generated for different gantry angles (e.g., every 10 degrees), as described herein.

Detection and assignment of the phases or states of the cycle 800 may be done using imaging. For example, a 4D CT or MRI may be used to identify each of the phases of a cycle for the patient. After identification, a plan may be developed for the phases or states for the particular patient (e.g., based on size of target, location of target at each phase, location of other tissue, etc.).

Figure 9:
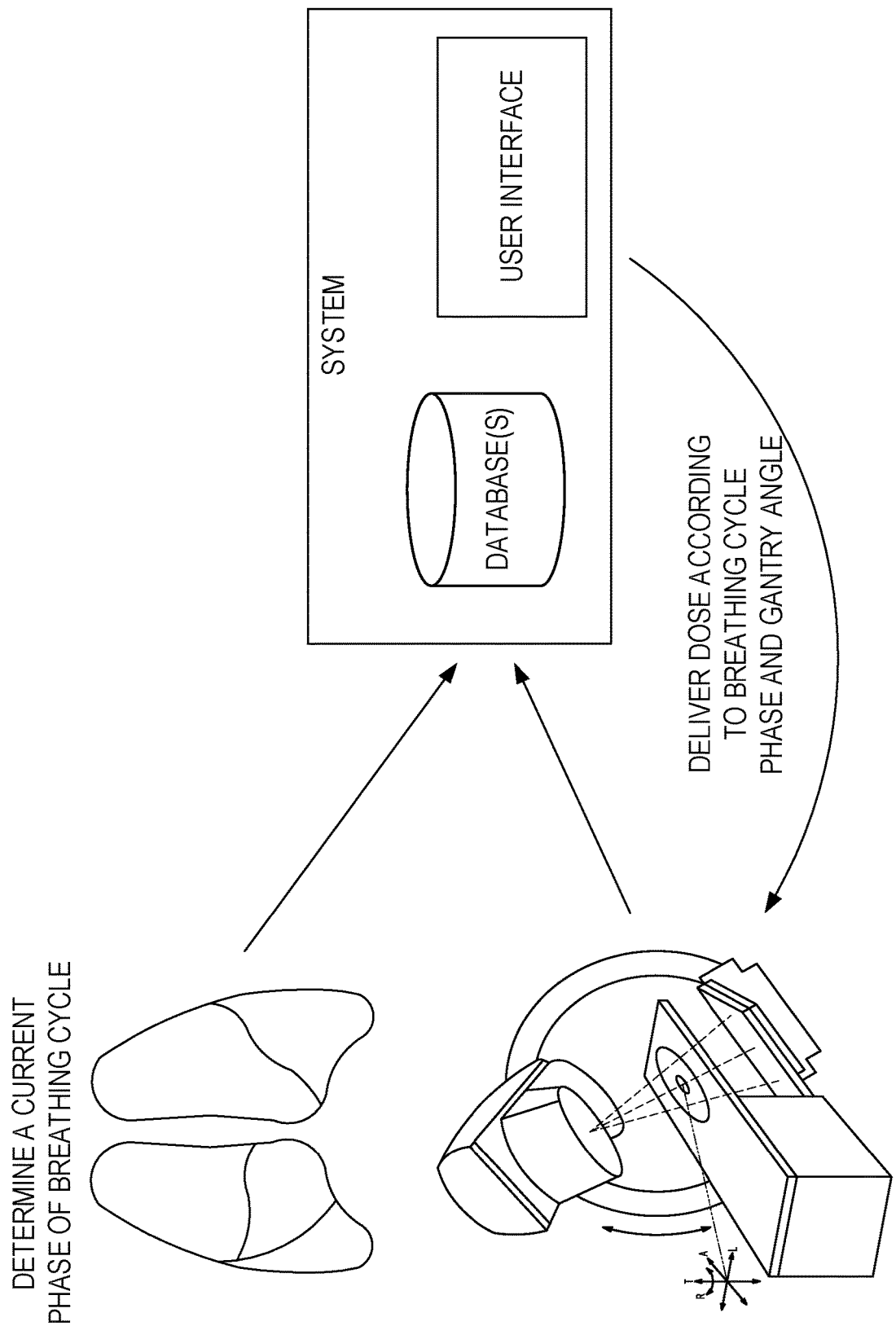
FIG. 9 illustrates a diagram showing selection of a radiation dose according to a breathing cycle and a gantry angle.

FIG. 9 illustrates a diagram showing selection of a radiation dose according to a breathing cycle and a gantry angle. The selection of the radiation dose may include determining a current phase or state of a breathing cycle and identifying a current gantry angle. Radiation dosage corresponding to these two variables may be stored in a database of a system, for example with a radiation dosage for each pair of unique phases and gantry angles. In an example, a nearest gantry angle may be used (e.g., rounded to the nearest 1, 5, 10, etc., degrees). The radiation dose may be specific to a target of the patient for the phase and gantry angle (or range) or to a layer of the target. The particular dose may be sent to a controller to deliver the dose using the gantry.

The dose may be delivered by a continuously rotating gantry. The patient phase and gantry angle may change as the gantry rotates, and other radiation doses may be used, for example every degree or range of degrees. In an example, the radiation dose is to be identified every 10 degrees of rotation. For example, the radiation dose may be used from 0 to 10 degrees, with the plan generated according to the position of the gantry at 5 degrees (e.g., a central degree of the range). The dose indicated may be delivered while the gantry rotates from 0 to 10 degrees, or changed according to the phase change (but using the gantry angle of 5 degrees throughout this range). The radiation dose may be saved in a database, with a lookup including variables of phase and gantry angle used to query the corresponding gantry angle and patient state.

Figure 10A:
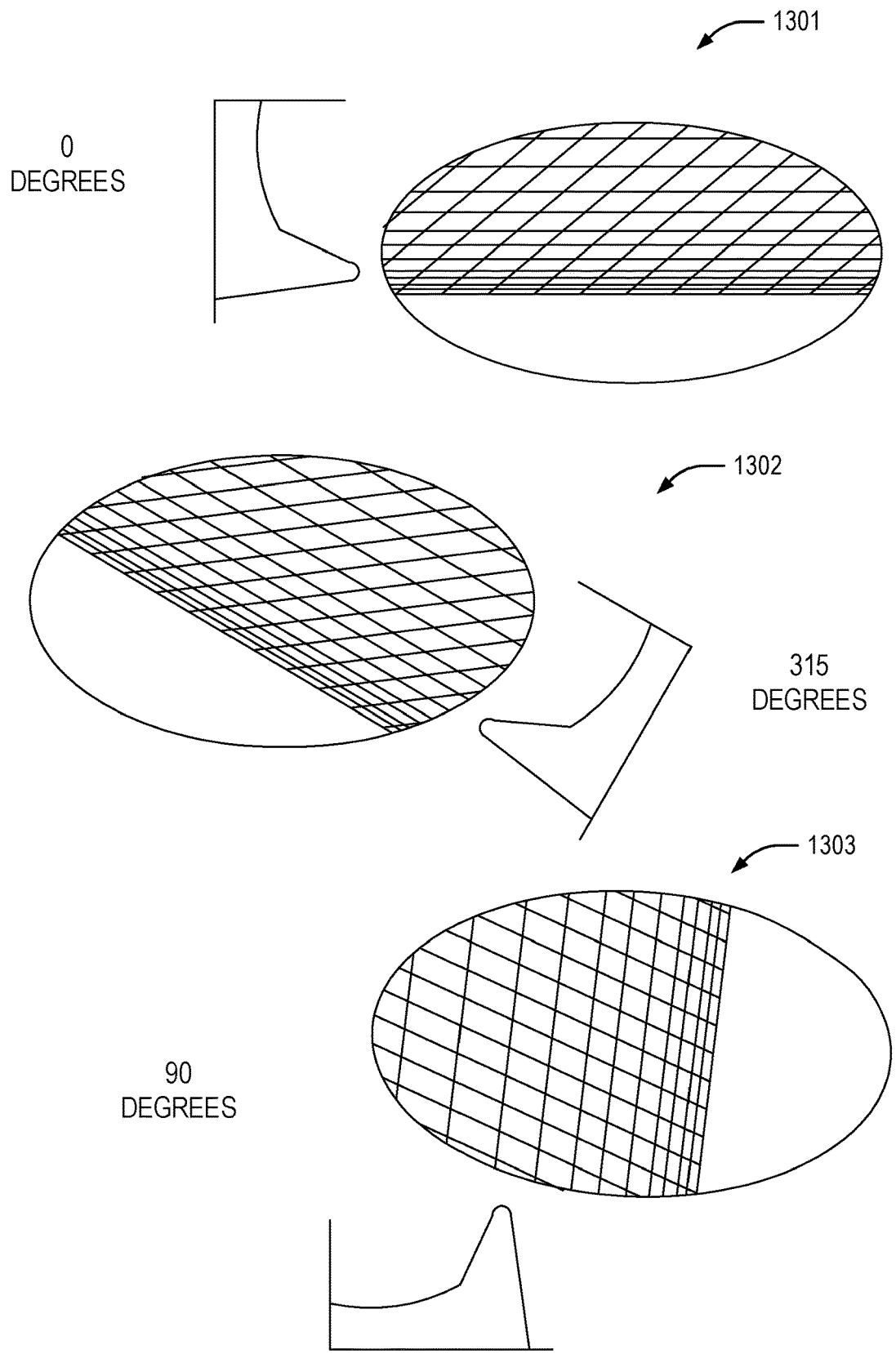
FIG. 10A illustrate arc angle target location intensity and Bragg peaks for various angles, in accordance with an embodiment.

FIG. 10A illustrates arc angle target location intensity and Bragg peaks for various angles, in accordance with an embodiment. The angles show how the penetration of the particle beam has different intensity and distance according to the angle of the gantry.

Increasing the number of angles that multiple doses to the targeted tumor may be provided allows for any given region of the body that is not a targeted tumor to receive a smaller dose. By using a large number of angles, the statistical error of stopping power as well as any error in patient positioning may be reduced because these errors may be made to cancel each other by averaging of overlapping doses. Thus, by providing a good dose distribution even in the face of errors in positioning or stopping power, the proton therapy is more robust.

The rotating gantry may compensate for increased dosage in a center of the target by using techniques such as planning the spiral to "end" and restart at somewhere other than the center of the target on that plane. As shown in FIG. 10A, different angles produce different penetration depths and by having them end at not quite the center of the target, over dosing the patient may be avoided. Decreasing the intensity of beamlets closer to the center along the line perpendicular to the isocentric line and along the direction of motion of the gantry may provide similar and more precise compensation.

Figure 10B:
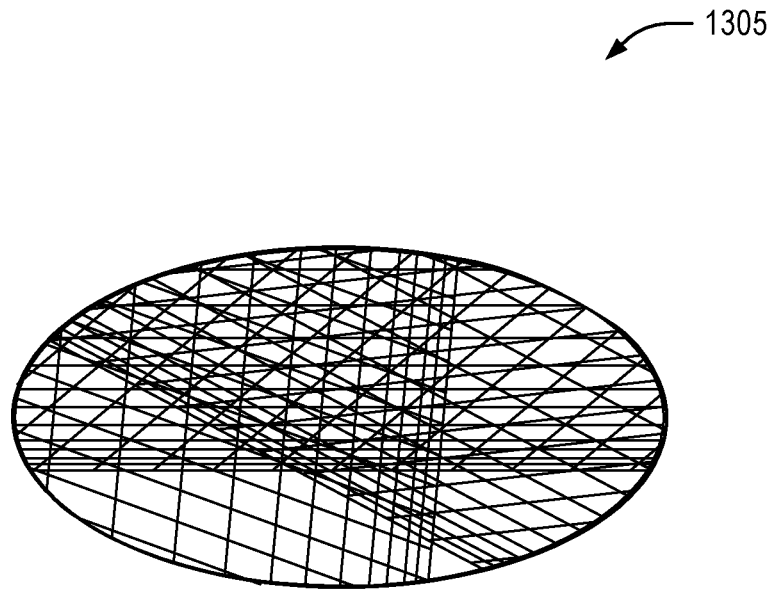
FIG. 10B illustrates a composite target location intensity, in accordance with an embodiment.

FIG. 10B illustrates a composite target location intensity, in accordance with an embodiment. The composite image shows how some overlap occurs among the different angles, but the overlap is minimized by not having all of the angles penetrate to the same depth in the target.

Proton arc therapy delivered using pencil beam scanning provides the ability to deliver distinct energies, where the change in energies may occur in less than one second. Pencil beam scanning enables intensity modulated proton therapy (IMPT), The selection of energies is very important because the selection of energies controls the depth of the radiation therapy treatment. Particle therapy inherently stops at a certain depth for a particular energy. This allows for the depth of treatment into a region of tissue to be layered. For each layer, the outline of the treatment may conform to a particular region of tissue; thereby allowing the outline to vary for the tumor from layer to layer, which is ideal for irregularly shaped tumors that are near organs at risk. When delivering from a rotating gantry there is limited time for delivering using multiple energies to distinct layers. The selection of energies at a given angle is important because it controls the depth at which the majority of the dose is delivered into the tumor. A system is able to achieve a desired aggregate dose to the tumor and do so in a timely fashion by judicious selection of a very limited number of energies for each angle. The system is able to ensure that the tumor is wholly irradiated by choosing energies that deliver past the midline of the tumor from a given angle. It is the aggregate dose to the tumor from all of the angles that is of clinical significance.

The accumulation of actual doses delivered is important for adaptive therapy. In an example, the parameters are optimized to achieve a desired dose to the target and to minimize the difference between the actual dose to the target from the prescribed dose to the target. The difference may be due to motion, and the actual dose to normal tissue may be different (e.g., greater) than the calculated dose. Knowing the actual dose distribution for a current session is important when there is an interruption in the delivery of the dose. On interruption of therapy, the dose may be recalculated based on the amount of dose delivered prior to the session being interrupted. In an example, the session may be restarted after interruption using the techniques described herein (e.g., by identifying a current breathing phase and a current gantry angle).

The dose distribution may be recalculated based on a set of parameters and the dose previously delivered. To determine the dose, the recalculation uses each gantry angle for the delivery of the particles, uses an identity of the breath phase associated with each gantry angle, and uses a subset of an image (e.g., a 4D CT or MRI) for the particular breath phase. A sum of all doses delivered using these weighted terms may be generated to determine an overall actual dose delivered. The actual dose may be an estimate.

When considering the breathing phase, the dose delivered may be determined based on a set of parameters including dosage delivered corresponding to pairs of breathing phase and gantry angles. In an example, the set of gantry angles and breath phase may be used to index back to the dose calculations initially performed prior to treatment. Summing the individual doses given the particular angle and breath phase combination results in a rapid approximation of the dose.

The breathing phase dosage reconstruction may differ from non-rotational delivery dosage reconstruction. For a non-rotational delivery, the plurality of layers aggregate cover the entire target. For a rotational delivery, the layers may be just one or two layers which are just past the middle of the target or just prior to the middle of the target (e.g., one layer of each). Thus, the layers shown in FIG. 10B illustrate a combination of layers directed to just past the middle of the target. Other examples may include a layer directed to just before the middle of the target.

In an example, the dose may be recalculated based on the actual parameters that were selected at each angle and breath phase. Using a continuously rotating gantry and based on a breathing phase, treatment may result in a dose to normal tissue (and organ at risk) that is not the same as any one of the sets of parameters (for a given breath phase) nor a weighted sum of the doses for all of the breath phrases. The accumulation of actual doses delivered may be important for adaptive therapy, and the current session dose distribution may be important in the event of an interrupted delivery (e.g., to continue delivery from the angle at which delivery was interrupted or to restart at a later time or date, which may be more difficult without knowing the angle and phase, as well as the delivery dosage actually delivered).

In an example, the dosage may be calculated based on the actual parameters incorporating the identification of the breath phase and using the subset of the 4D CT image for that breath phase. For example, a rapid approximation of the dose using actual parameters may be generated using the set of gantry angles and breath phase to index back to the dose calculations initially performed prior to treatment, and summing the individual doses given the particular angle and breath phase combination. The total dosage information may be useful as the patient changes weight or the tumor shrinks (or grows), to modify a treatment plan or further plan treatment.

Figure 11:
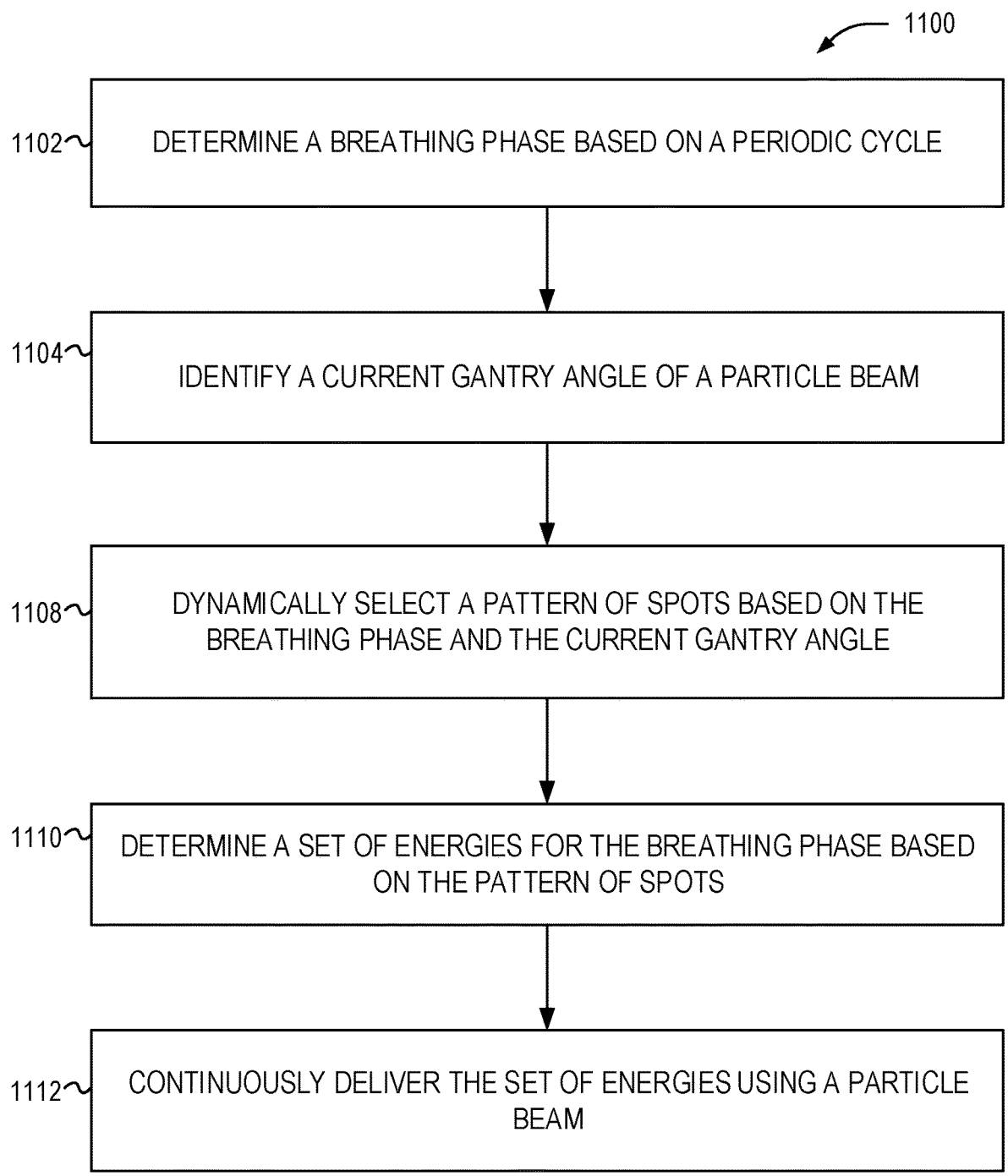
FIGS. 11-13 illustrate flowcharts showing techniques for delivering a particle beam towards a target based on a periodic cycle, in accordance with an embodiment.
Figure 12:
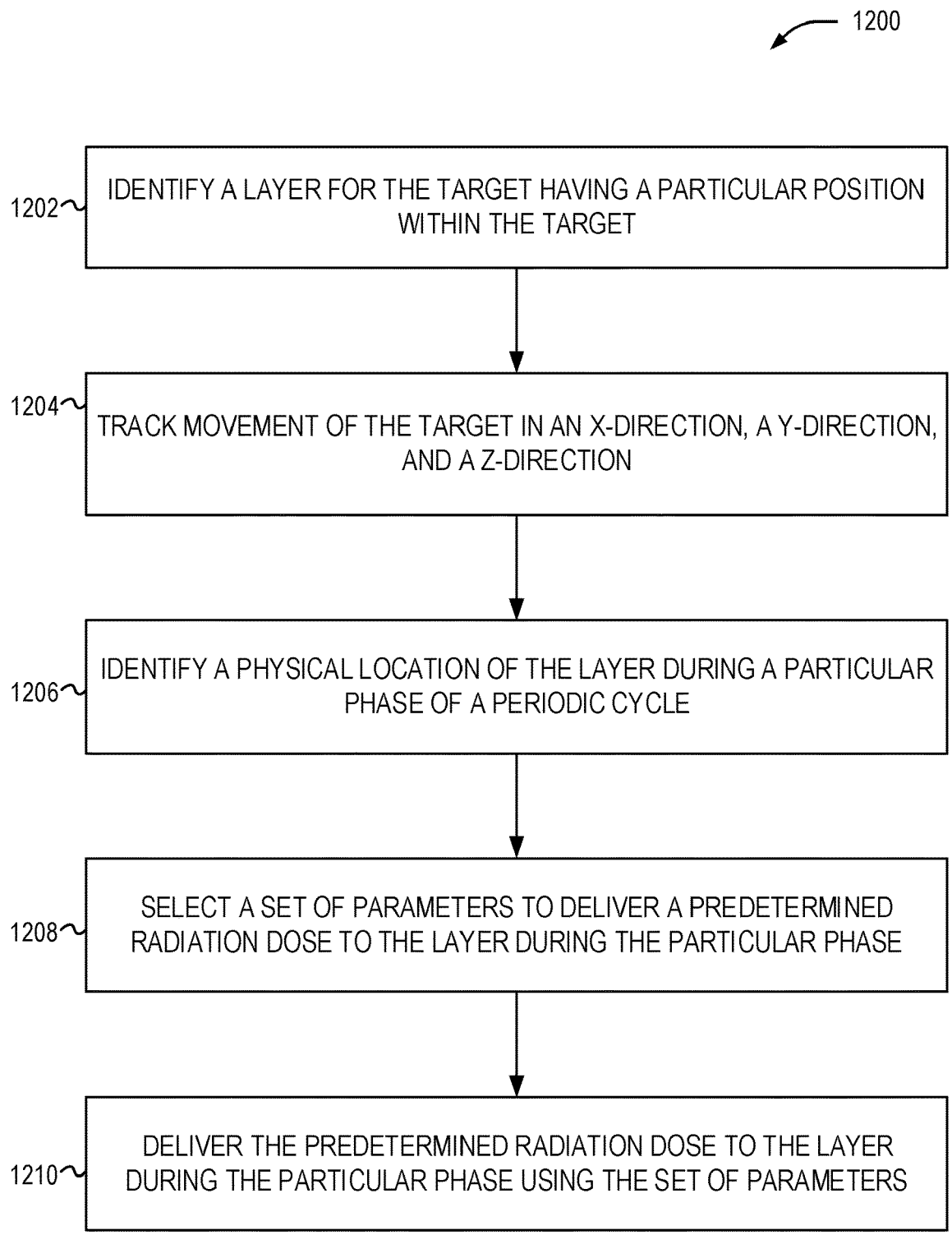
Figure 13:
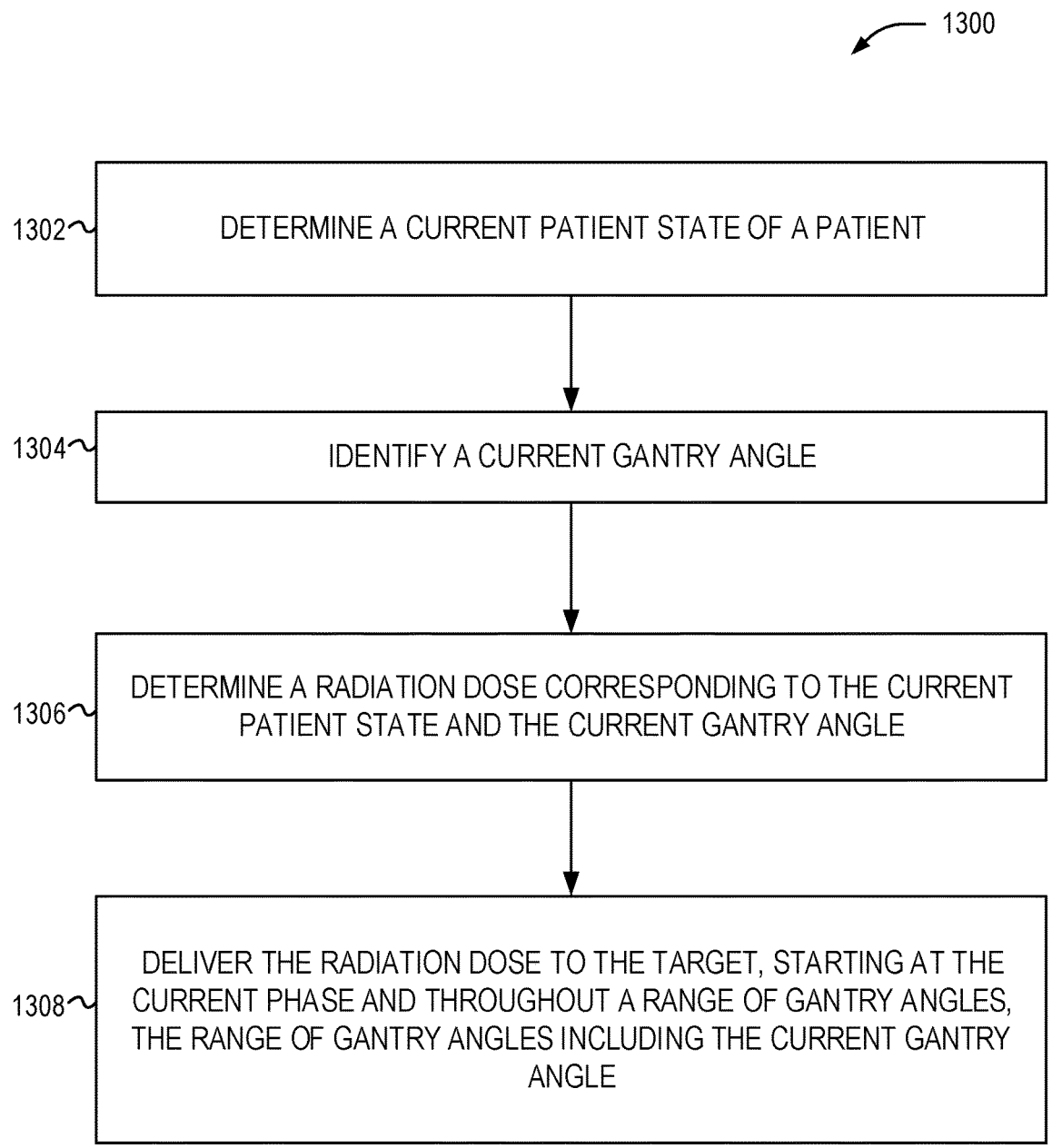

FIGS. 11-13 illustrate flowcharts showing techniques for delivering a particle beam towards a target based on a periodic cycle, in accordance with an embodiment.

FIG. 11 illustrates a technique 1100 for delivering a particle beam towards a target based on a periodic cycle, including an operation 1102 to determine a breathing phase based on the periodic cycle. The periodic cycle may include a breathing cycle, for example with 8 or 16 breathing phases. The technique 1100 includes an operation 1104 to identify a current gantry angle of the particle beam.

The technique 1100 includes an operation 1108 to dynamically select a pattern of spots based on the breathing phase and the current gantry angle. The technique 1100 includes an operation 1110 to determine a set of energies (e.g., beamlets) for the breathing phase based on the pattern of spots.

The technique 1100 includes an operation 1112 to continuously deliver the set of energies using the particle beam. The set of beamlets may be delivered from a rotating gantry (e.g., a continuously rotating gantry) towards the target. The technique 1100 may include determining a radiation dose based on a set of selected parameters for a particular gantry location, wherein at least one parameter is an angle and a breath phrase.

In an example, energy may be determined based on something similar to a radiological path length to the layer of the target intended and the intensity of the individual beamlets may be determined based on how much dose is to be delivered to an individual spot. The energy choice may differ based on the breath phase, such as when the (equivalent of) radiological path length varies, while the spot pattern may remain substantially similar and have substantially similar intensities. Or the energy may stay the same with the spot pattern changing with intensities varying, such as due to lateral motion of the tumor with respect to the central beam axis. The set of beamlets may include energy changes or spot pattern changes over time while being delivered to the target.

FIG. 12 illustrates a technique 1200 for delivering a particle beam at a particular gantry angle towards a moving target, wherein the particle beam is delivered based on a set of control points. The technique 1200 includes an operation 1202 to identify a layer for the target having a particular position within the target. In an example, the set of parameters include a beam energy, the beam energy traveling to a predefined depth into the target for the layer. In an example, the set of parameters include a spot size.

In an example, the set of parameters may include a plurality of beamlets, each beamlet having a different intensity. The intensity may include a number of particles delivered. Each beamlet in this example may have a particular coordinate location. The technique 1200 may further include wherein a first beamlet of the plurality of beamlets has a first intensity for the layer at a first phase of the periodic cycle, a second beamlet of the plurality of beamlets has a second intensity for the layer at a second phase of the periodic cycle, and a third beamlet of the plurality of beamlets has a third intensity for a second layer at the first phase of the periodic cycle.

The technique 1200 includes an operation 1204 to track movement of the target in an x-direction, a y-direction, and a z-direction. The technique 1200 includes an operation 1206 to identify a physical location of the layer during a particular phase of a periodic cycle. In an example, the particular phase is a breathing phase of a respiratory breathing cycle.

The technique 1200 includes an operation 1208 to select a set of parameters to deliver a predetermined radiation dose to the layer during the particular phase. In an example, the set of parameters selected may include a particular gantry angle or range of gantry angles. The technique 1200 includes an operation 1210 to deliver the predetermined radiation dose to the layer during the particular phase using the set of parameters. The predetermined radiation dose may be delivered at the particular gantry angle.

The technique 1200 may include iterating through a plurality of target layers at respective breathing phases and gantry angles until each target layer has received its respective predetermined dose. The technique 1200 may include verifying the delivery of the radiation dose to each of the specified target layers or to the target as a whole. Verifying the delivery of the radiation dose may include determining that the correct meterset has been delivered. In another example, verifying the delivery may include determining an estimate of an actual intended dose received by the target compared to a prescribed dose. The estimate of the actual intended dose may be determined using an external measurement (e.g., a 4D CT scan). The technique 1200 may include delivering a different radiation dose at a physical location of the layer during different phases of the periodic cycle.

FIG. 13 illustrates a technique 1300 for delivering a particle beam towards a target based on a periodic cycle, including an operation 1302 to determine a current patient state of a patient. The current patient state may be a phase of the periodic cycle. In an example, the phase is a breathing phase and the periodic cycle is a breathing cycle having 8 or 16 breathing phases. In an example, the patient state includes at least one of a breathing phase, an approximation of a breathing phase, an amplitude, a deformation vector field (DVF), a low-dimensional representation of a DVF, a low-dimensional representation of images acquired with an imaging device, surface information, a target position, or the like The technique 1300 includes an operation 1304 to identify a current gantry angle.

The technique 1300 includes an operation 1306 to determine a radiation dose corresponding to the current patient state and the current gantry angle.

The technique 1300 includes an operation 1308 to deliver the radiation dose to the target, starting at the current patient state and throughout a range of gantry angles, the range of gantry angles including the current gantry angle. For example, the range of gantry angles may include a 10 degrees range, with a central angle being the current gantry angle.

The technique 1300 may include iterating through a plurality of ranges of gantry angles at respective patient states until the target has received its predetermined dose. In an example, this operation may include determining an estimate of an actual intended dose received by the target by reconstructing a dose given for each of the plurality of ranges of gantry angles. The operation may further include determining the estimate using a weighted sum of the dose given for each of the plurality of ranges of gantry angles.

The technique 1300 may further include an operation for determining, for the current gantry angle, a plurality of predefined spots in the target, wherein the plurality of predefined spots are configured in a spiral pattern. This operation may include ordering the plurality of predefined spots in the spiral pattern from those closest to an isocentric axis for the respective gantry angle to those most distant from the isocentric axis. Delivering the predetermined radiation dose may include delivering a plurality of beamlets according to the spiral pattern of the plurality of predefined spots.

The technique 1300 may further include restarting delivery of the predetermined radiation dose at a particular gantry angle when delivery is interrupted at the particular gantry angle. The delivery may be restarted using a radiation dose corresponding to the particular gantry angle and a new current patient state.

The radiation dose described herein may include a plurality of beamlets. The plurality of beamlets may include a first beamlet having a first intensity for the target at a first patient state of the periodic cycle, a second beamlet having a second intensity for the target at a second patient state of the periodic cycle. In an example, the patient state may be a breathing phase calculated from a respiratory cycle.

Each of the non-limiting examples described in this document may stand on its own, or may be combined in various permutations or combinations with one or more of the other examples.

Example 1 is a method of delivering a particle beam towards a target based on a periodic cycle, the method comprising: determining a breathing phase based on the periodic cycle; identifying a current gantry angle of the particle beam; dynamically selecting a pattern of spots based on the breathing phase and the current gantry angle; and determining a set of beamlets based on the pattern of spots; and continuously delivering the set of beamlets using the particle beam.

In Example 2, the subject matter of Example 1 includes, wherein delivering the set of beamlets further comprises delivering the set of beamlets from a rotating gantry towards the target.

In Example 3, the subject matter of Example 2 includes, determining a radiation dose based on a set of selected parameters for the current gantry angle, wherein at least one parameter is an angle and a breath phrase.

Example 4 is a method of delivering a particle beam at a particular gantry angle towards a moving target, wherein the particle beam is delivered based on a set of control points, the method comprising: identifying a layer for the target having a particular position within the target; tracking movement of the target in an x-direction, a y-direction, and a z-direction; identifying a physical location of the layer during a particular phase of a periodic cycle; selecting a set of parameters to deliver a predetermined radiation dose to the layer during the particular phase and at a particular gantry angle; and delivering the predetermined radiation dose to the layer during the particular phase and at the particular gantry angle, using the set of parameters.

In Example 5, the subject matter of Example 4 includes, iterating through a plurality of target layers at respective breathing phases and gantry angles until each target layer has received its respective predetermined dose.

In Example 6, the subject matter of Examples 4-5 includes, wherein a radiation dose to be delivered differs at the physical location of the layer during different phases of the periodic cycle.

In Example 7, the subject matter of Examples 4-6 includes, wherein the set of parameters include a beam energy, the beam energy traveling to a predefined depth into the target for the layer.

In Example 8, the subject matter of Examples 4-7 includes, wherein the set of parameters include a spot size.

In Example 9, the subject matter of Examples 4-8 includes, wherein the set of parameters include a plurality of beamlets, each beamlet having a different intensity, wherein the intensity is the number of particles delivered and each beamlet has a particular coordinate location.

In Example 10, the subject matter of Example 9 includes, wherein a first beamlet of the plurality of beamlets has a first intensity for the layer at a first phase of the periodic cycle, a second beamlet of the plurality of beamlets has a second intensity for the layer at a second phase of the periodic cycle, and a third beamlet of the plurality of beamlets has a third intensity for a second layer at the first phase of the periodic cycle.

In Example 11, the subject matter of Examples 4-10 includes, wherein the periodic cycle is a respiratory breathing cycle.

Example 12 is a method of delivering a particle beam towards a target, the method comprising: determining a current patient state of a patient; identifying a current gantry angle; determining a radiation dose corresponding to the current patient state and the current gantry angle; and delivering the radiation dose to the target, starting at the current patient state and throughout a range of gantry angles, the range of gantry angles including the current gantry angle.

In Example 13, the subject matter of Example 12 includes, iterating through a plurality of ranges of gantry angles at respective patient states until the target has received its predetermined dose.

In Example 14, the subject matter of Example 13 includes, determining an estimate of an actual intended dose received by the target by reconstructing a dose given for each of the plurality of ranges of gantry angles.

In Example 15, the subject matter of Example 14 includes, determining the estimate using a weighted sum of the dose given for each of the plurality of ranges of gantry angles.

In Example 16, the subject matter of Examples 12-15 includes, wherein the current gantry angle is a central angle of the range of gantry angles.

In Example 17, the subject matter of Examples 12-16 includes, for the current gantry angle, determining a plurality of predefined spots in the target, wherein the plurality of predefined spots are configured in a spiral pattern; and ordering the plurality of predefined spots in the spiral pattern from those closest to an isocentric axis for the respective gantry angle to those most distant from the isocentric axis; and wherein delivering the radiation dose includes delivering a plurality of beamlets according to the spiral pattern of the plurality of predefined spots.

In Example 18, the subject matter of Examples 12-17 includes, wherein the radiation dose includes a plurality of beamlets, and wherein a first beamlet of the plurality of beamlets has a first intensity for the target at a first patient state of the periodic cycle, a second beamlet of the plurality of beamlets has a second intensity for the target at a second patient state of the periodic cycle.

In Example 19, the subject matter of Examples 12-18 includes, wherein the patient state includes at least one of a breathing phase, an approximation of a breathing phase, an amplitude, a deformation vector field (DVF), a low-dimensional representation of a DVF, a low-dimensional representation of images acquired with an imaging device, surface information, or a target position.

In Example 20, the subject matter of Examples 12-19 includes, wherein the patient state is a breathing phase calculated from a respiratory cycle.

Example 21 is a system for delivering a particle beam towards a target based on a periodic cycle, the system comprising: one or more processors coupled to a memory device, the memory device containing instructions that, when executed by the one or more processors, cause the system to: determine a breathing phase based on the periodic cycle; identify a current gantry angle of the particle beam; dynamically select a pattern of spots based on the breathing phase and the current gantry angle; and determine a set of beamlets based on the pattern of spots; and cause the particle beam to continuously deliver the set of beamlets.

In Example 22, the subject matter of Example 21 includes, wherein delivering the set of beamlets further comprises delivering the set of beamlets from a rotating gantry towards the target.

In Example 23, the subject matter of Example 22 includes, wherein the instructions further cause the one or more processors to determine a radiation dose based on a set of selected parameters for the current gantry angle, wherein at least one parameter is an angle and a breath phrase.

Example 24 is a system for delivering a particle beam at a particular gantry angle towards a moving target, wherein the particle beam is delivered based on a set of control points, the system comprising: one or more processors coupled to a memory device, the memory device containing instructions that, when executed by the one or more processors, cause the system to: identify a layer for the target having a particular position within the target; track movement of the target in an x-direction, a y-direction, and a z-direction; identify a physical location of the layer during a particular phase of a periodic cycle; select a set of parameters to deliver a predetermined radiation dose to the layer during the particular phase and at a particular gantry angle; and cause the predetermined radiation dose to be delivered to the layer during the particular phase and at the particular gantry angle, using the set of parameters.

In Example 25, the subject matter of Example 24 includes, wherein the instructions further cause the one or more processors to iterate through a plurality of target layers at respective breathing phases and gantry angles until each target layer has received its respective predetermined dose.

In Example 26, the subject matter of Examples 24-25 includes, wherein a radiation dose to be delivered differs at the physical location of the layer during different phases of the periodic cycle.

In Example 27, the subject matter of Examples 24-26 includes, wherein the set of parameters include a beam energy, the beam energy traveling to a predefined depth into the target for the layer.

In Example 28, the subject matter of Examples 24-27 includes, wherein the set of parameters include a spot size.

In Example 29, the subject matter of Examples 24-28 includes, wherein the set of parameters include a plurality of beamlets, each beamlet having a different intensity, wherein the intensity is the number of particles delivered and each beamlet has a particular coordinate location.

In Example 30, the subject matter of Example 29 includes, wherein a first beamlet of the plurality of beamlets has a first intensity for the layer at a first phase of the periodic cycle, a second beamlet of the plurality of beamlets has a second intensity for the layer at a second phase of the periodic cycle, and a third beamlet of the plurality of beamlets has a third intensity for a second layer at the first phase of the periodic cycle.

In Example 31, the subject matter of Examples 24-30 includes, wherein the periodic cycle is a respiratory breathing cycle.

Example 32 is a system of delivering a particle beam towards a target, the system comprising: one or more processors coupled to a memory device, the memory device containing instructions that, when executed by the one or more processors, cause the system to: determine a current patient state of a patient; identify a current gantry angle; determine a radiation dose corresponding to the current patient state and the current gantry angle; and cause the radiation dose to be delivered to the target, starting at the current patient state and throughout a range of gantry angles, the range of gantry angles including the current gantry angle.

In Example 33, the subject matter of Example 32 includes, wherein the instructions further cause the one or more processors to iterate through a plurality of ranges of gantry angles at respective patient states until the target has received its predetermined dose.

In Example 34, the subject matter of Example 33 includes, wherein the instructions further cause the one or more processors to determine an estimate of an actual intended dose received by the target by reconstructing a dose given for each of the plurality of ranges of gantry angles.

In Example 35, the subject matter of Example 34 includes, wherein the instructions further cause the one or more processors to determine the estimate using a weighted sum of the dose given for each of the plurality of ranges of gantry angles.

In Example 36, the subject matter of Examples 32-35 includes, wherein the current gantry angle is a central angle of the range of gantry angles.

In Example 37, the subject matter of Examples 32-36 includes, wherein the instructions further cause the one or more processors to: for the current gantry angle, determine a plurality of predefined spots in the target, wherein the plurality of predefined spots are configured in a spiral pattern; and order the plurality of predefined spots in the spiral pattern from those closest to an isocentric axis for the respective gantry angle to those most distant from the isocentric axis; and wherein delivering the radiation dose includes delivering a plurality of beamlets according to the spiral pattern of the plurality of predefined spots.

In Example 38, the subject matter of Examples 32-37 includes, wherein the radiation dose includes a plurality of beamlets, and wherein a first beamlet of the plurality of beamlets has a first intensity for the target at a first patient state of the periodic cycle, a second beamlet of the plurality of beamlets has a second intensity for the target at a second patient state of the periodic cycle.

In Example 39, the subject matter of Examples 32-38 includes, wherein the patient state includes at least one of a breathing phase, an approximation of a breathing phase, an amplitude, a deformation vector field (DVF), a low-dimensional representation of a DVF, a low-dimensional representation of images acquired with an imaging device, surface information, or a target position.

In Example 40, the subject matter of Examples 32-39 includes, wherein the patient state is a breathing phase calculated from a respiratory cycle.

Example 41 is a machine readable medium including instructions for delivering a particle beam towards a target based on a periodic cycle, which, when executed by one or more processors, cause the one or more processors to perform operations to: determine a breathing phase based on the periodic cycle; identify a current gantry angle of the particle beam; dynamically select a pattern of spots based on the breathing phase and the current gantry angle; determine a set of beamlets based on the pattern of spots; and cause the particle beam to continuously deliver the set of beamlets.

In Example 42, the subject matter of Example 41 includes, wherein delivering the set of beamlets further comprises delivering the set of beamlets from a rotating gantry towards the target.

In Example 43, the subject matter of Example 42 includes, wherein the instructions further cause the one or more processors to determine a radiation dose based on a set of selected parameters for the current gantry angle, wherein at least one parameter is an angle and a breath phrase.

Example 44 is a machine readable medium including instructions for delivering a particle beam at a particular gantry angle towards a moving target, wherein the particle beam is delivered based on a set of control points, which, when executed by one or more processors, cause the one or more processors to perform operations to: identify a layer for the target having a particular position within the target; track movement of the target in an x-direction, a y-direction, and a z-direction; identify a physical location of the layer during a particular phase of a periodic cycle; select a set of parameters to deliver a predetermined radiation dose to the layer during the particular phase and at a particular gantry angle; and cause the predetermined radiation dose to be delivered to the layer during the particular phase and at the particular gantry angle, using the set of parameters.

In Example 45, the subject matter of Example 44 includes, wherein the instructions further cause the one or more processors to iterate through a plurality of target layers at respective breathing phases and gantry angles until each target layer has received its respective predetermined dose.

In Example 46, the subject matter of Examples 44-45 includes, wherein a radiation dose to be delivered differs at the physical location of the layer during different phases of the periodic cycle.

In Example 47, the subject matter of Examples 44-46 includes, wherein the set of parameters include a beam energy, the beam energy traveling to a predefined depth into the target for the layer.

In Example 48, the subject matter of Examples 44-47 includes, wherein the set of parameters include a spot size.

In Example 49, the subject matter of Examples 44-48 includes, wherein the set of parameters include a plurality of beamlets, each beamlet having a different intensity, wherein the intensity is the number of particles delivered and each beamlet has a particular coordinate location.

In Example 50, the subject matter of Example 49 includes, wherein a first beamlet of the plurality of beamlets has a first intensity for the layer at a first phase of the periodic cycle, a second beamlet of the plurality of beamlets has a second intensity for the layer at a second phase of the periodic cycle, and a third beamlet of the plurality of beamlets has a third intensity for a second layer at the first phase of the periodic cycle.

In Example 51, the subject matter of Examples 44-50 includes, wherein the periodic cycle is a respiratory breathing cycle.

Example 52 is a machine readable medium including instructions for delivering a particle beam towards a target, which, when executed by one or more processors, cause the one or more processors to perform operations to: determine a current patient state of a patient; identify a current gantry angle; determine a radiation dose corresponding to the current patient state and the current gantry angle; and cause the radiation dose to be delivered to the target, starting at the current patient state and throughout a range of gantry angles, the range of gantry angles including the current gantry angle.

In Example 53, the subject matter of Example 52 includes, wherein the instructions further cause the one or more processors to iterate through a plurality of ranges of gantry angles at respective patient states until the target has received its predetermined dose.

In Example 54, the subject matter of Example 53 includes, wherein the instructions further cause the one or more processors to determine an estimate of an actual intended dose received by the target by reconstructing a dose given for each of the plurality of ranges of gantry angles.

In Example 55, the subject matter of Example 54 includes, wherein the instructions further cause the one or more processors to determine the estimate using a weighted sum of the dose given for each of the plurality of ranges of gantry angles.

In Example 56, the subject matter of Examples 52-55 includes, wherein the current gantry angle is a central angle of the range of gantry angles.

In Example 57, the subject matter of Examples 52-56 includes, wherein the instructions further cause the one or more processors to: for the current gantry angle, determine a plurality of predefined spots in the target, wherein the plurality of predefined spots are configured in a spiral pattern; and order the plurality of predefined spots in the spiral pattern from those closest to an isocentric axis for the respective gantry angle to those most distant from the isocentric axis; and wherein delivering the radiation dose includes delivering a plurality of beamlets according to the spiral pattern of the plurality of predefined spots.

In Example 58, the subject matter of Examples 52-57 includes, wherein the radiation dose includes a plurality of beamlets, and wherein a first beamlet of the plurality of beamlets has a first intensity for the target at a first patient state of the periodic cycle, a second beamlet of the plurality of beamlets has a second intensity for the target at a second patient state of the periodic cycle.

In Example 59, the subject matter of Examples 52-58 includes, wherein the patient state includes at least one of a breathing phase, an approximation of a breathing phase, an amplitude, a deformation vector field (DVF), a low-dimensional representation of a DVF, a low-dimensional representation of images acquired with an imaging device, surface information, or a target position.

In Example 60, the subject matter of Examples 52-59 includes, wherein the patient state is a breathing phase calculated from a respiratory cycle.

Example 61 is at least one machine-readable medium including instructions that, when executed by processing circuitry, cause the processing circuitry to perform operations to implement of any of Examples 1-60.

Example 62 is an apparatus comprising means to implement of any of Examples 1-60.

Example 63 is a system to implement of any of Examples 1-60.

Example 64 is a method to implement of any of Examples 1-60.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The invention claimed is:

1. A method of delivering a particle beam towards a target based on a periodic cycle, the method comprising:
    determining a current breathing phase based on the periodic cycle, the breathing phase determined from a set of breathing phases of the periodic cycle, and the breathing phase indicating a location of the target;
    identifying a current gantry angle of the particle beam;
    dynamically selecting a pattern of spots having particular sizes including a first size and a second size, based on the breathing phase and the current gantry angle, from a set of spot patterns corresponding to each of the set of breathing phases at the current gantry angle; and
    determining a set of beamlets based on the pattern of spots, wherein a respective beamlet of the set of beamlets has a diameter corresponding to a size of a respective spot for delivery, the set of beamlets including at least one beamlet having a first diameter corresponding to the first size and selected to be delivered at a first spot of the pattern of spots, and at least one beamlet having a second diameter corresponding to the second size and selected to be delivered at a second spot of the pattern of spots, the second diameter different than the first diameter; and
    continuously delivering, without gating, at least a portion of the set of beamlets to the target using the particle beam over a range of gantry angles including the current gantry angle, wherein the particle beam is delivered continuously throughout a radiation session along a plurality of ranges of gantry angles including the range of gantry angles.

2. The method of claim 1, wherein delivering the set of beamlets further comprises delivering the set of beamlets from a rotating gantry towards the target.

3. The method of claim 2, further comprising determining a radiation dose based on a set of selected parameters for the current gantry angle, wherein at least one parameter is an angle and a breath phrase.

4. A method of delivering a particle beam at a particular gantry angle towards a moving target, wherein the particle beam is delivered based on a set of control points, the method comprising:
    identifying a layer for the target having a particular position within the target;
    tracking movement of the target in an x-direction, a y-direction, and a z-direction;
    identifying a physical location of the layer during a current particular phase of a periodic cycle, the particular phase determined from a set of phases of the periodic cycle;
    selecting a set of parameters to deliver a predetermined radiation dose to the layer during the particular phase and at a particular gantry angle, the set of parameters selected from a group of parameter sets corresponding to each of the set of phases at the particular gantry angle, wherein the predetermined radiation dose includes a set of beamlets including at least one beamlet having a first diameter corresponding to a first size specified in the set of parameters and selected to be delivered at a first portion of the physical location, and at least one beamlet having a second diameter corresponding to a second size specified in the set of parameters and selected to be delivered at a second portion of the physical location, the second diameter different than the first diameter; and
    continuously delivering, without gating, at least a portion of the predetermined radiation dose to the layer during the particular phase and over a range of gantry angles including the particular gantry angle, using the set of parameters, wherein the particle beam is delivered continuously throughout a radiation session along a plurality of ranges of gantry angles including the range of gantry angles.

5. The method of claim 4, further comprising iterating through a plurality of target layers at respective breathing phases and gantry angles until each target layer has received its respective predetermined dose delivered continuously.

6. The method of claim 4, wherein a radiation dose to be delivered differs at the physical location of the layer during different phases of the periodic cycle.

7. The method of claim 4, wherein the set of parameters include a beam energy, the beam energy traveling to a predefined depth into the target for the layer.

8. The method of claim 4, wherein the set of parameters include a spot size.

9. The method of claim 4, wherein the set of parameters include a plurality of beamlets, each beamlet having a different intensity, wherein the intensity is the number of particles delivered and each beamlet has a particular coordinate location.

10. The method of claim 9, wherein a first beamlet of the plurality of beamlets has a first intensity for the layer at a first phase of the periodic cycle, a second beamlet of the plurality of beamlets has a second intensity for the layer at a second phase of the periodic cycle, and a third beamlet of the plurality of beamlets has a third intensity for a second layer at the first phase of the periodic cycle.

11. The method of claim 4, wherein the periodic cycle is a respiratory breathing cycle.

12. A method of delivering a particle beam towards a target, the method comprising:

determining a current patient state of a patient, the current patient state determined from a set of patient states of a periodic cycle, and the current patient state indicating a location of the target;

identifying a current gantry angle;

determining a radiation dose corresponding to the current patient state and the current gantry angle, the radiation dose selected from a set of radiation doses corresponding to each of the set of patient states at the current gantry angle, wherein the radiation dose includes a set of beamlets including at least one beamlet having a first diameter selected to be delivered at a first portion of the target and at least one beamlet having a second diameter selected to be delivered at a second portion of the target, the second diameter different than the first diameter; and continuously delivering, without gating, at least a portion of the radiation dose to the target, starting at the current patient state and throughout a range of gantry angles, the range of gantry angles including the current gantry angle, wherein the particle beam is delivered continuously throughout a radiation session along a plurality of ranges of gantry angles including the range of gantry angles.

13. The method of claim 12, further comprising iterating continuously through a plurality of ranges of gantry angles at respective patient states until the target has received its predetermined dose.

14. The method of claim 13, further comprising determining an estimate of an actual dose received by the target by reconstructing a dose given for each of the plurality of ranges of gantry angles.

15. The method of claim 14, further comprising determining the estimate using a weighted sum of the dose given for each of the plurality of ranges of gantry angles.

16. The method of claim 12, wherein the current gantry angle is a central angle of the range of gantry angles.

17. The method of claim 12, further comprising:

for the current gantry angle, determining a plurality of predefined spots in the target, wherein the plurality of predefined spots are configured in a spiral pattern; and ordering the plurality of predefined spots in the spiral pattern from those closest to an isocentric axis for the respective gantry angle to those most distant from the isocentric axis; and wherein delivering the radiation dose includes delivering a plurality of beamlets according to the spiral pattern of the plurality of predefined spots.

18. The method of claim 12, wherein the radiation dose includes a plurality of beamlets, and wherein a first beamlet of the plurality of beamlets has a first intensity for the target at a first patient state of the periodic cycle, a second beamlet of the plurality of beamlets has a second intensity for the target at a second patient state of the periodic cycle.

19. The method of claim 12, wherein the patient state includes at least one of a breathing phase, an approximation of a breathing phase, an amplitude, a deformation vector field (DVF), a low-dimensional representation of a DVF, a low-dimensional representation of images acquired with an imaging device, surface information, or a target position.

20. The method of claim 12, wherein the patient state is a breathing phase calculated from a respiratory cycle.

21. The method of claim 17, wherein the plurality of predefined spots are ordered in the spiral pattern with a clockwise direction for the range of gantry angles and wherein a second plurality of predefined spots are ordered in a spiral pattern with a counterclockwise direction for a second range of gantry angles.

22. The method of claim 17, wherein the plurality of predefined spots include a first set of spots having a first spot size and a second set of spots having a second spot size, the first spot size larger than the second spot size and wherein each of the first set of spots are located closer to the isocentric axis than each of the second set of spots.

* * * * *